US012572182B2

(12) United States Patent
Jang et al.

(10) Patent No.: US 12,572,182 B2
(45) Date of Patent: Mar. 10, 2026

(54) WEARABLE ELECTRONIC DEVICE COMPRISING DAMPING STRUCTURE OF CIRCUIT BOARD

(71) Applicant: Samsung Electronics Co., Ltd., Suwon-si (KR)

(72) Inventors: Dongheon Jang, Suwon-si (KR); Junghyun Kang, Suwon-si (KR); Taegyun Kim, Suwon-si (KR); Sanghwa Lee, Suwon-si (KR); Seongho Hong, Suwon-si (KR); Chungsoon Park, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 219 days.

(21) Appl. No.: 18/352,580

(22) Filed: Jul. 14, 2023

(65) Prior Publication Data

US 2024/0036612 A1 Feb. 1, 2024

Related U.S. Application Data

(63) Continuation of application No. PCT/KR2023/009589, filed on Jul. 6, 2023.

(30) Foreign Application Priority Data

Jul. 28, 2022 (KR) ........................ 10-2022-0093634
Aug. 5, 2022 (KR) ........................ 10-2022-0097837

(51) Int. Cl.
G06F 1/16 (2006.01)
A61B 5/00 (2006.01)
(Continued)

(52) U.S. Cl.
CPC .............. G06F 1/1658 (2013.01); A61B 5/00 (2013.01); F16F 15/04 (2013.01); G04G 17/04 (2013.01);
(Continued)

(58) Field of Classification Search
CPC .......... G06F 1/1658; G06F 1/16; G06F 1/163; A61B 5/00; A61B 5/681; F16F 15/04;
(Continued)

(56) References Cited

U.S. PATENT DOCUMENTS 5,750,272 A * 5/1998 Jardine ................. F16F 15/005
428/668
6,937,479 B2 * 8/2005 Anderson ............. B81B 7/0048
257/668
(Continued)

FOREIGN PATENT DOCUMENTS

CN 215771551 U 2/2022
CN 217011151 U 7/2022
(Continued)

OTHER PUBLICATIONS

International Search Report dated Oct. 24, 2023, issued in International Patent Application No. PCT/KR2023/009589.
(Continued)

*Primary Examiner* — Allen L Parker
*Assistant Examiner* — Martin Antonio Asmat Uceda
(74) *Attorney, Agent, or Firm* — Jefferson IP Law, LLP

(57) ABSTRACT

A wearable electronic device is provided. The wearable device includes a bracket, a printed circuit board that at least partially faces a first surface of the bracket, a sound sensor structure disposed on a second surface of the bracket, a biometric sensor structure that overlaps the first surface of the bracket with respect to a direction that is perpendicular to the printed circuit board and a damping structure interposed between the biometric sensor structure and the printed circuit board. The damping structure may elastically support the biometric sensor structure and the printed circuit board.

19 Claims, 9 Drawing Sheets

(51) Int. Cl.

| | |
|---|---|
| *F16F 15/04* | (2006.01) |
| *G04G 17/04* | (2006.01) |
| *H04R 1/28* | (2006.01) |
| *H05K 1/02* | (2006.01) |
| *H05K 1/18* | (2006.01) |
| *H05K 1/181* | (2026.01) |

(52) U.S. Cl.

CPC ............... *G06F 1/16* (2013.01); *G06F 1/163* (2013.01); *H04R 1/2876* (2013.01); *H05K 1/0271* (2013.01); *H05K 1/181* (2013.01); *H05K 2201/10015* (2013.01); *H05K 2201/10151* (2013.01)

(58) Field of Classification Search

CPC .... G04G 17/04; H04R 1/2876; H05K 1/0271; H05K 1/181; H05K 2201/10015; H05K 2201/10151; B81B 7/0058; G01D 11/10

See application file for complete search history.

(56) References Cited

U.S. PATENT DOCUMENTS

| | | | | |
|---|---|---|---|---|
| 8,584,525 | B2 * | 11/2013 | Offterdinger | .......... G01D 11/10 |
| | | | | 73/526 |
| 9,208,774 | B2 | 12/2015 | Hardell | |
| 9,582,034 | B2 * | 2/2017 | von Badinski | ......... G06F 21/32 |
| 9,596,756 | B2 * | 3/2017 | Rainer | ................... H05K 3/284 |
| 9,756,157 | B2 * | 9/2017 | Iwamoto | ............ H04M 1/0262 |
| 9,798,356 | B2 * | 10/2017 | Nakayama | .......... H01M 50/136 |
| 10,133,389 | B2 | 11/2018 | Shim et al. | |
| 10,216,274 | B2 * | 2/2019 | Chapeskie | .............. G06F 3/017 |
| 10,297,909 | B2 * | 5/2019 | Kim | ........................ H01Q 1/273 |
| 10,431,382 | B2 * | 10/2019 | Li | ........................... H01G 4/30 |
| 10,627,861 | B2 * | 4/2020 | Connor | ................... G06F 3/017 |
| 10,682,094 | B2 * | 6/2020 | Kim | ........................ G04G 21/02 |
| 10,866,619 | B1 * | 12/2020 | Bushnell | ............... G06F 1/1656 |
| 10,988,375 | B1 * | 4/2021 | English | ................. B81B 7/0016 |
| 11,140,770 | B2 * | 10/2021 | Chiu | ........................ H01G 2/06 |
| 11,314,268 | B2 | 4/2022 | Han et al. | |
| 11,348,358 | B2 | 5/2022 | Kim et al. | |
| 11,432,766 | B2 * | 9/2022 | Pandya | .............. A61B 5/02405 |
| 11,487,380 | B2 | 11/2022 | Lee et al. | |
| 11,504,057 | B2 * | 11/2022 | Clavelle | ............. A61B 5/02438 |
| 11,583,200 | B2 | 2/2023 | Han et al. | |
| 11,960,249 | B2 * | 4/2024 | Kim | ....................... H02J 7/0042 |
| 12,174,660 | B2 * | 12/2024 | Chang | ................... G06F 1/1656 |
| 2008/0264169 | A1 * | 10/2008 | Ingrisch | ................ B60T 8/3675 |
| | | | | 73/514.14 |
| 2010/0242605 | A1 * | 9/2010 | Offterdinger | ........ G01D 11/245 |
| | | | | 73/514.38 |
| 2014/0055974 | A1 * | 2/2014 | Hansen | .................. H05K 1/144 |
| | | | | 361/804 |
| 2014/0139454 | A1 * | 5/2014 | Mistry | .................... G06F 3/017 |
| | | | | 345/173 |

| | | | | |
|---|---|---|---|---|
| 2014/0196541 | A1 * | 7/2014 | Hofsaess | ................ G01D 3/036 |
| | | | | 29/831 |
| 2014/0307889 | A1 | 10/2014 | Hardell | |
| 2015/0070864 | A1 | 3/2015 | Rainer et al. | |
| 2015/0173675 | A1 * | 6/2015 | Shimizu | .................. A61B 5/721 |
| | | | | 600/595 |
| 2015/0186092 | A1 * | 7/2015 | Francis | ................... G06F 21/35 |
| | | | | 345/520 |
| 2015/0208933 | A1 | 7/2015 | Satomi et al. | |
| 2015/0286277 | A1 * | 10/2015 | Kim | ........................ G06F 1/163 |
| | | | | 345/156 |
| 2016/0058375 | A1 * | 3/2016 | Rothkopf | ............ G04G 21/025 |
| | | | | 600/323 |
| 2016/0065655 | A1 * | 3/2016 | Bentley | ................... H04L 67/10 |
| | | | | 709/201 |
| 2016/0091921 | A1 * | 3/2016 | Lee | .......................... G06F 1/163 |
| | | | | 250/372 |
| 2017/0032168 | A1 * | 2/2017 | Kim | ..................... H04L 63/0861 |
| 2017/0033335 | A1 * | 2/2017 | Kojima | ............... H01M 50/211 |
| 2017/0064811 | A1 * | 3/2017 | Li | ........................... H05K 3/284 |
| 2017/0180850 | A1 * | 6/2017 | Hsu | ........................ H04R 1/028 |
| 2017/0281081 | A1 * | 10/2017 | Nousiainen | ........ A61B 5/02427 |
| 2018/0024684 | A1 | 1/2018 | Shim et al. | |
| 2018/0116532 | A1 * | 5/2018 | Han | ........................ G06F 1/163 |
| 2018/0220923 | A1 * | 8/2018 | Shim | ...................... A61B 5/742 |
| 2018/0317787 | A1 | 11/2018 | Satomi et al. | |
| 2019/0302953 | A1 | 10/2019 | Lee et al. | |
| 2020/0004291 | A1 * | 1/2020 | Wexler | ................... G10L 15/10 |
| 2020/0209903 | A1 | 7/2020 | Han et al. | |
| 2020/0278719 | A1 * | 9/2020 | Starnes | ................... H04R 3/04 |
| 2020/0323489 | A1 | 10/2020 | Kim et al. | |
| 2021/0153810 | A1 * | 5/2021 | Min | ....................... G01N 21/35 |
| 2021/0312154 | A1 | 10/2021 | Kim et al. | |
| 2022/0187869 | A1 | 6/2022 | Han et al. | |
| 2023/0083928 | A1 | 3/2023 | Lee et al. | |
| 2024/0019812 | A1 * | 1/2024 | Lee | ....................... G06F 3/0362 |
| 2024/0040757 | A1 * | 2/2024 | Jung | ....................... H04M 1/02 |
| 2024/0348093 | A1 * | 10/2024 | Lee | ......................... G06F 1/163 |

FOREIGN PATENT DOCUMENTS

| | | | | |
|---|---|---|---|---|
| KR | 20180046762 | A | * | 5/2018 |
| KR | 10-2019-0115159 | | | 10/2019 |
| KR | 10-2020-0083023 | A | | 7/2020 |
| KR | 10-2020-0120407 | A | | 10/2020 |
| KR | 10-2022-0017192 | A | | 2/2022 |
| KR | 10-2022-0099365 | A | | 7/2022 |
| KR | 10-2022-0102089 | A | | 7/2022 |
| WO | 2018/080170 | A2 | | 5/2018 |

OTHER PUBLICATIONS

Extended European Search Report dated Jul. 23, 2025, issued in a European Patent Application No. 23846856.5.

* cited by examiner

900

WEARABLE ELECTRONIC DEVICE COMPRISING DAMPING STRUCTURE OF CIRCUIT BOARD

CROSS-REFERENCE TO RELATED APPLICATION(S)

This application is a continuation application, claiming priority under § 365 (c), of an International application No. PCT/KR2023/009589, filed on Jul. 6, 2023, which is based on and claims the benefit of a Korean patent application number 10-2022-0093634, filed on Jul. 28, 2022, in the Korean Intellectual Property Office, and of a Korean patent application number 10-2022-0097837, filed on Aug. 5, 2022, in the Korean Intellectual Property Office, the disclosure of each of which is incorporated by reference herein in its entirety.

TECHNICAL FIELD

The disclosure relates to a wearable electronic device.

BACKGROUND ART

Wearable electronic devices, such as smart watches, have become public. Such a wearable electronic device may include a printed circuit board. Various elements, such as a capacitor, may be mounted on the printed circuit board of the wearable electronic device. The capacitor may be expanded and/or contracted by a voltage applied for an operation. Vibrations may occur due to expansion and/or contraction of the capacitor. However, it is not admitted that the above-described related art is a prior art.

The above information is presented as background information only to assist with an understanding of the disclosure. No determination has been made, and no assertion is made, as to whether any of the above might be applicable as prior art with regard to the disclosure.

DISCLOSURE

Technical Solution

Aspects of the disclosure are to address at least the above-mentioned problems and/or disadvantages and to provide at least the advantages described below. Accordingly, an aspect of the disclosure is to provide a wearable electronic device.

Additional aspects will be set forth in part in the description which follows and, in part, will be apparent from the description, or may be learned by practice of the presented embodiments.

In accordance with an aspect of the disclosure, a wearable electronic device is provided. The wearable device includes a housing including a cover. The wearable electronic device may include a bracket disposed in the housing and including a first part. The wearable electronic device may include a printed circuit board that is disposed between the cover and the bracket and at least partially faces a first surface of the first part of the bracket. The wearable electronic device may include a sound sensor structure disposed on a second surface that is different from the first surface of the first part of the bracket. The wearable electronic device may include a biometric sensor structure installed in the cover to overlap the first surface of the first part of the bracket with respect to a direction that is perpendicular to the printed circuit board. The wearable electronic device may include a damping structure interposed between the biometric sensor structure and the printed circuit board and configured to elastically support the biometric sensor structure and the printed circuit board.

In accordance with another aspect of the disclosure, a wearable electronic device is provided. The electronic device includes a housing including a cover. The wearable electronic device may include a bracket disposed in the housing and including a first part. The wearable electronic device may include a printed circuit board that is disposed between the cover and the bracket and at least partially faces a first surface of the first part of the bracket. The wearable electronic device may include a sound sensor structure disposed on a second surface that is different from the first surface of the first part of the bracket. The wearable electronic device may include a damping structure. The cover may include a protrusion that extends toward the printed circuit board. The damping structure may be disposed between the printed circuit board and the protrusion.

Other aspects, advantages, and salient features of the disclosure will become apparent to those skilled in the art from the following detailed description, which, taken in conjunction with the annexed drawings, discloses various embodiments of the disclosure.

DESCRIPTION OF DRAWINGS

The above and other aspects, features, and advantages of certain embodiments of the disclosure will be more apparent from the following description taken in conjunction with the accompanying drawings, in which.

Throughout the drawings, it should be noted that like reference numbers are used to depict the same or similar elements, features, and structures.

MODE FOR INVENTION

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Figure 1:
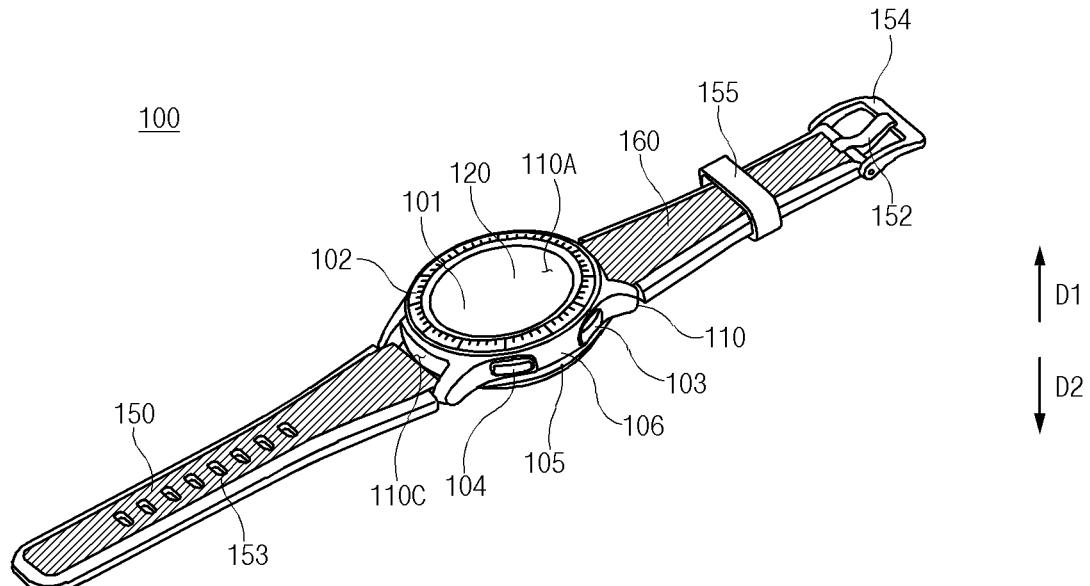
FIG. 1 is a perspective view of a wearable electronic device according to an embodiment of the disclosure.

FIG. 1 is a perspective view of a wearable electronic device according to an embodiment of the disclosure.

Figure 2:
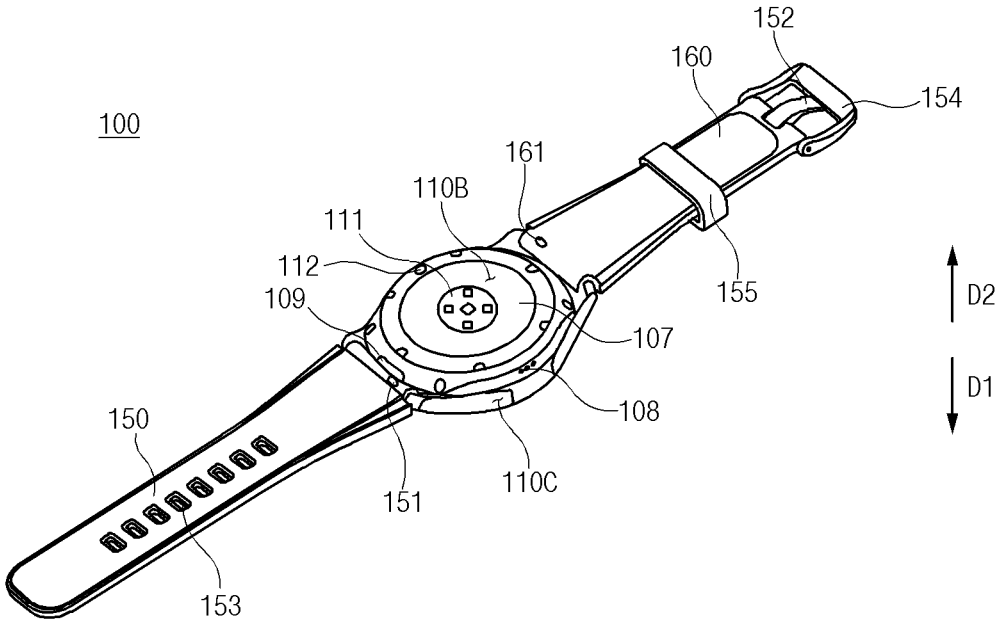
FIG. 2 is a perspective view of a wearable electronic device according to an embodiment of the disclosure.

FIG. 2 is a perspective view of a wearable electronic device according to an embodiment of the disclosure.

Hereinafter, a first direction D1 and a second direction D2 may be defined with reference to a wearable electronic device. The first direction D1 may be a direction that faces a front cover 101 from a rear cover 107. The first direction may be a direction that is substantially perpendicular to the front cover 101. The second direction D2 may be a direction that is opposite to the first direction D1.

Referring to FIGS. 1 and 2, a wearable electronic device 100 (e.g., an electronic device 901 of FIG. 9) according to an embodiment may include a housing 110 and fastening members 150 and 160.

The housing 110 may at least partially define an external appearance of the wearable electronic device 100. For example, the housing 110 may include a first surface (or a front surface) 110A that defines an external appearance of the electronic device 100, a second surface (or a rear surface) 110B, and a side surface that surrounds a space between the first surface 110A and the second surface 110B. The housing 110 may be referenced by a structure that defines at least a portion of the first surface 110A, the second surface 110B, and the side surface 110C. The fastening members 150 and 160 may be connected to the housing 110 and may be configured to detachably fasten the wearable electronic device 100 to a portion (e.g., a wrist or the like) of a body of a user.

At least a portion of the first surface 110A that faces the first direction D1 may be defined by a substantially transparent front cover 101. The front cover 101, for example, may include a glass plate including various coating layers, a polymer plate, or a combination thereof. The front cover 101 may be substantially plate-shaped, but the disclosure is not limited thereto.

The second surface 110B that faces the second direction D2 may be defined by the rear cover 107. The rear cover 107 may include a substantially transparent area and/or a substantially opaque area. The rear cover 107, for example, may be formed of coated or colored glass, ceramics, a polymer, a metal (aluminum, stainless steel (STS), or magnesium), or a combination of at least two of the materials.

The side surface 110C may be formed at least partially by a frame 106. The frame 106 may be coupled to the front cover 101 and the rear cover 107. The frame 106, for example, may include a metal and/or a polymer. The frame 106 may be referenced as a frame structure, a side bezel structure, or a side member.

The fastening members 150 and 160 may be formed of various materials and forms. For example, the fastening members 150 and 160 may be formed of a woven article, leather, rubber, urethane, a metal, ceramics, or a combination of at least two of the materials.

The wearable electronic device 100 according to an embodiment may include a display 120, audio modules 105 and 106, a first sensor module 111, a second sensor module 112, key input devices 102, 103, and 104, and a connector hole 109.

The display 120 may be exposed through a considerable part of the front cover 101. For example, the display 120 may be visually viewed through the transparent area of the front cover 101. A form of the display 120 may be a form corresponding to a form of the front cover 101, and for example, may be various forms, such as a circular form, an elliptical form, or a polygonal form. The wearable electronic device 100 may include a touch detecting circuit that is coupled to the display 120 and/or is disposed adjacent to the display 120, a pressure sensor that may measure an intensity (pressure) of a touch, and/or a fingerprint sensor.

The audio modules 105 and 108 may include a microphone hole 105 and a speaker hole 108. A microphone for acquiring external sounds may be disposed in an interior of the microphone hole 105. The microphone hole 105 may include a plurality of microphones to detect a direction of a sound, but the disclosure is not limited thereto. The speaker hole 108 may be used as an external speaker or a voice communication receiver. In an embodiment of the disclosure, the speaker hole 108 and the microphone hole 105 may be implemented by one or a plurality of holes, but a speaker with no speaker hole 108 may be used (e.g., a piezoelectric speaker). In an embodiment of the disclosure, the speaker hole 108 and/or the microphone hole 105 may have a grill form having a plurality of openings, but the disclosure is not limited thereto.

The first sensor module 111 and the second sensor module 112 may generate electrical signals or data values corresponding to an operation state of an interior of the wearable electronic device 100 or an external environment state. The first sensor module 111 and the second sensor module 112 may be disposed on the rear surface of the rear cover 107. The first sensor module 111, for example, may include a heart rate monitor (HRM) sensor, but the disclosure is not limited thereto. The second sensor module 112, for example, may include a temperature sensor, but the disclosure is not limited thereto. The wearable electronic device 100 may include a sensor module that is not illustrated, for example, at least one of a gesture sensor, a gyro sensor, an atmospheric pressure sensor, a magnetic sensor, an acceleration sensor, a grip sensor, a color sensor, a humidity sensor, or an illumination intensity sensor.

The key input devices 102, 103, and 104 may include a wheel key 102 that is disposed on the first surface 110A of the housing 110 and may be rotated in at least one direction, and/or side key buttons 103 and 104 that are disposed on the side surface 110C of the housing 110. The wheel key may have a form corresponding to the form of the front cover 101. In an embodiment of the disclosure, the wearable electronic device 100 may not include some or all of the above-mentioned key input devices 102, 103, and 104 or may further include another key input device that is not illustrated. At least some of the key input devices 102, 103, and 104 may be implemented in another form, such as a soft key, on the display 120.

The connector hole 109 may accommodate a connector (e.g., a USB connector) for transmitting and/or receiving electric power and/or data to and from an external electronic device, or may accommodate a connector (e.g., an earphone connector) for transmitting and/or receiving an audio signal to and from the external electronic device. However, the wearable electronic device 100 may not include the connector hole 109. However, a function (e.g., transmission and reception of electrical signals using wired communication) using the connector hole 109 may be performed at least partially by a wireless communication module (e.g., a wireless communication module 992 of FIG. 9) of the wearable electronic device 100.

The fastening members 150 and 160 may be connected to each other to be detached and/or fastened in at least a partial area of the housing 110 by using locking members 151 and 161. The fastening members may include one or more of a fixing member 152, a fixing member coupling hole 153, a band guide member 154, a band fixing ring 155.

The fixing member 152 may be configured to fix the housing 110 and the fastening members 150 and 160 to a portion (e.g., a wrist and the like) of a body of a user. The fixing member coupling hole 153 may fix the housing 110 and the fastening members 150 and 160 to the portion of the body of the user in correspondence to the fixing member 152. The band guide member 154 may be configured to restrict a movement range of the fixing member 152 when the fixing member 152 is coupled to the fixing member coupling hole 153 to allow the fastening members 150 and 160 to be adhered to the portion of the body of the user. The band fixing ring 155 may restrict movement ranges of the fastening members 150 and 160 in a state, in which the fixing member 152 and the fixing member coupling hole 153 are coupled to each other. However, configurations, such as the fixing member 152 and the fixing member coupling hole 153 of the fastening members 150 and 160, for fastening the wearable electronic device 100 to the body of the user are not limited to the above-described example, and various mechanisms may be applied.

Figure 3:
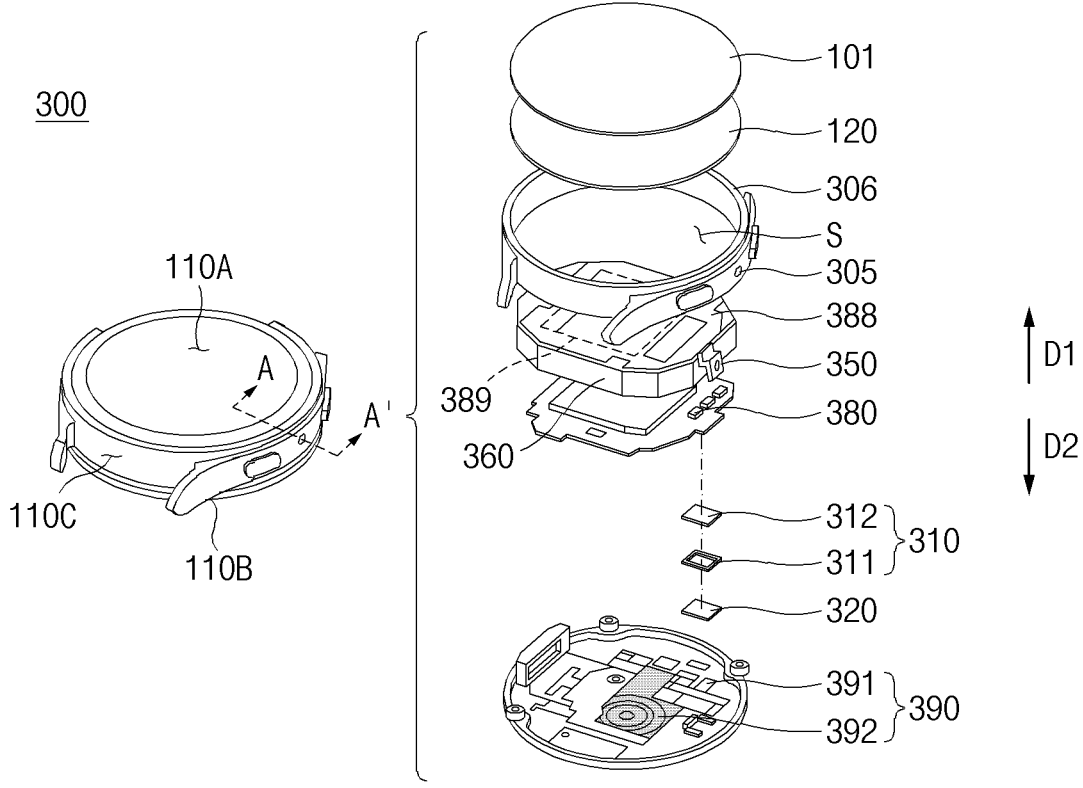
FIG. 3 is an exploded perspective view of a wearable electronic device according to an embodiment of the disclosure.

FIG. 3 is an exploded perspective view of a wearable electronic device according to an embodiment of the disclosure.

Referring to FIG. 3, a wearable electronic device 300 (e.g., the wearable electronic device 100 of FIG. 1) according to an embodiment may include the front cover 101, a rear cover 390, a frame 306, the display 120, a bracket 360, a battery 389, a support plate 388, a sound sensor structure 350 (or a sound sensor module), a printed circuit board 380, a biometric sensor structure 320 (or a biometric sensor module), and a damping structure 310.

The front cover 101 may be disposed at an upper portion (e.g., the first direction D1) of the frame 306. The front cover 101 may be coupled to the frame 306. The rear cover 390 may be disposed at a lower portion (e.g., the second direction D2) of the frame 306. The rear cover 390 may be coupled to the frame 306.

The rear cover 390 (e.g., the rear cover 107 of FIG. 2) may include a first cover 391 and a second cover 392. The first cover 391 may be coupled to the frame 306. For example, the first cover 391 may be coupled to the frame 306 under (e.g., the second direction D2) of the frame 306. The second cover 392 may be coupled to the first cover 391. For example, the second cover 392 may be coupled to the first cover 391 under (e.g., the second direction D2) of the frame 306. The second cover 392 may at least partially close a hollow formed in the first cover 391.

The first cover 391 and the second cover 392 may be formed of different materials. For example, the first cover 391 may include a resin and the second cover 392 may include glass, but the disclosure is not limited by the above-described example. Alternatively, the first cover 391 and the second cover 392 may be formed of substantially the same material. In this case, selectively, the first cover 391 and the second cover 392 may be integrally formed.

The frame 306 (e.g., the frame 106 of FIG. 1) may be disposed between the front cover 101 and the rear cover 390. The front cover 101, the rear cover 390, and the frame 306 may at least partially define an external appearance of the wearable electronic device 300. For example, the front cover 101, the rear cover 390, and the frame 306 may define at least a portion of the front surface 110A, the rear surface 110B, and the side surface 110C of the wearable electronic device 300. In this aspect, at least a portion of the front cover 101, the rear cover 390, and the frame 306 may be referenced as a housing (e.g., the housing 110 of FIG. 1) of the wearable electronic device 300.

The frame 306 may define an interior space "S" of the wearable electronic device 300, together with the front cover 101 and the rear cover 390. For example, the frame 306 may include a side wall that defines a hollow in an interior of the frame 306. The front cover 101 and the rear cover 390 may be coupled to upper and lower portions of the side wall of the frame 306, respectively, to at least partially close the hollow in the interior of the frame 306. By the front cover 101, the rear cover 390, and the frame 306 coupled to each other, the interior space "S" of the wearable electronic device 300 may be defined.

In the interior space "S", the display 120, the support plate 388, the bracket 360, the battery 389, the printed circuit board 380, the sound sensor structure 350, the biometric sensor structure 320, and the damping structure 310 may be disposed.

The display 120 may be disposed between the front cover 101 and the bracket 360 (or the support plate 388). The display 120 may be at least partially accommodated in the interior of the frame 306. The display 120 may be at least partially supported by the support plate 388 and the bracket 360. The display 120 may be attached to a rear surface (e.g., a surface that faces the second direction D2) of the front cover 101. For example, the display 120 may be attached to the front cover 101 by a substantially transparent bonding member (e.g., an optically clear adhesive (OCA) or an optically clear resin (OCR)).

The bracket 360 may be disposed in the interior of the frame 306. The bracket 360 may be surrounded by the frame 306. The display 120 may be disposed on a first side (e.g., the first direction D1) of the bracket 360. The printed circuit board 380 may be disposed on a second side (e.g., the second direction D2) of the bracket 360. The bracket 36—may support the display 120 and the printed circuit board 380. The bracket 360 may be referenced as a support member. The bracket 360, for example, may be formed of a metallic material and/or a nonmetallic material (e.g., a polymer, such as plastic).

The battery 389 may be at least partially accommodated in a space formed in the bracket 360. The battery 389 may be disposed between the support plate 388 and the printed circuit board 380. The battery 389 may store electric power that is to be supplied to at least one component of the wearable electronic device 300. The battery 389, for example, may include a rechargeable secondary battery.

The support plate 388 may be disposed on the bracket 360. The support plate 388 may cover the battery 389 accommodated in the bracket 360. The support plate 388 may support the battery 389 and the display 120. The support plate 388 may be formed of a metal, and may provide an electrical shied between the battery 389 and the display 120. The support plate 388, for example, may include stainless steel, but the disclosure is not limited thereto.

The sound sensor structure 350 may be installed in the bracket 360. For example, the sound sensor structure 350 may be disposed on a side surface of the bracket 360. The side surface of the bracket 360 may include an area (e.g., a second surface 361B of FIG. 5) that faces the frame 306 of the bracket 360. The sound sensor structure 350 may be located between the bracket 360 and the frame 306. The sound sensor structure 350 may face a microphone hole 305 (e.g., the microphone hole 105 of FIG. 1) formed in the frame 306. The sound sensor structure 350 may acquire a sound signal through the microphone hole 305.

The printed circuit board 380 may be disposed between the bracket 360 and the rear cover 390. A processor (e.g., a processor 920 of FIG. 9), a memory (e.g., a memory 930 of FIG. 9), and/or an interface (e.g., an interface 977 of FIG. 9) may be mounted on the printed circuit board 380. The processor, for example, may include one or more of a graphic processing unit (GPU), an application processor sensor, a sensor processor, or a communication processor. The memory, for example, may include a volatile memory or a nonvolatile memory. The interface, for example, may include a high definition multimedia interface (HDMI), a universal serial bus (USB) interface, an SD card interface, and/or an audio interface. The interface, for example, may include a USB connector, an SD card/MMC connector, or a connector (e.g., a connection terminal 978 of FIG. 9), such as an audio connector to electrically or physically connect the wearable electronic device 300 to an external electronic device.

The biometric sensor structure 320 (e.g., the second sensor module 112 of FIG. 2) may be installed on the rear cover 390. For example, the biometric sensor structure 320 may be installed in the first cover 391 of the rear cover 390. The biometric sensor structure 320 may be disposed on a rear surface (e.g., a surface that faces the first direction D1) of the first cover 391. The biometric sensor structure 320 installed in the rear cover 390 may acquire biometric information of a user who contacts or is adjacent to the rear cover 390.

The damping structure 310 may be disposed between the printed circuit board 380 and the biometric sensor structure 320. The damping structure 310 may include a first member 311 and a second member 312. The first member 311 may be disposed on the biometric sensor structure 320 (e.g., the first direction D1). The second member 312 may be disposed on the first member 311 (e.g., the first direction D1). The second member 312 may be disposed between the first member 311 and the printed circuit board 380. The first member 311 may have a ring shape having a hollow, but the disclosure is not limited thereto. For example, the first member 311 may have a plate shape that does no hollow.

Figure 4:
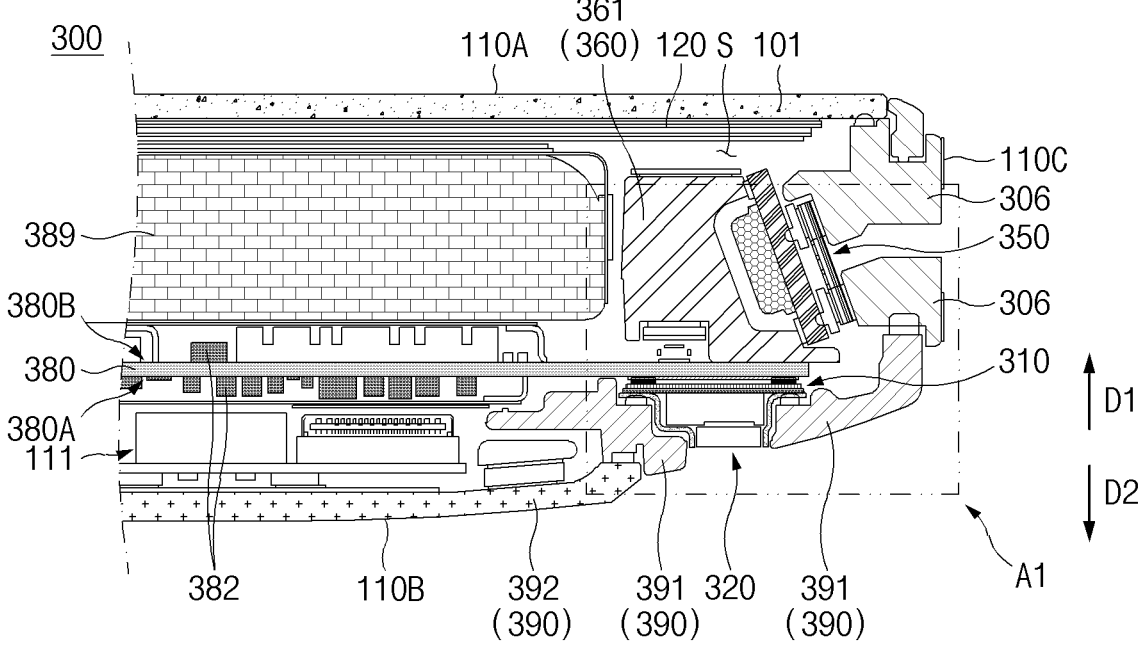
FIG. 4 is a cross-sectional view of a wearable electronic device according to an embodiment of the disclosure.

FIG. 4 is a cross-sectional view of a wearable electronic device according to an embodiment of the disclosure. The cross-sectional view of FIG. 4 may be a cross-sectional view taken along line A-A' of FIG. 3.

Figure 5:
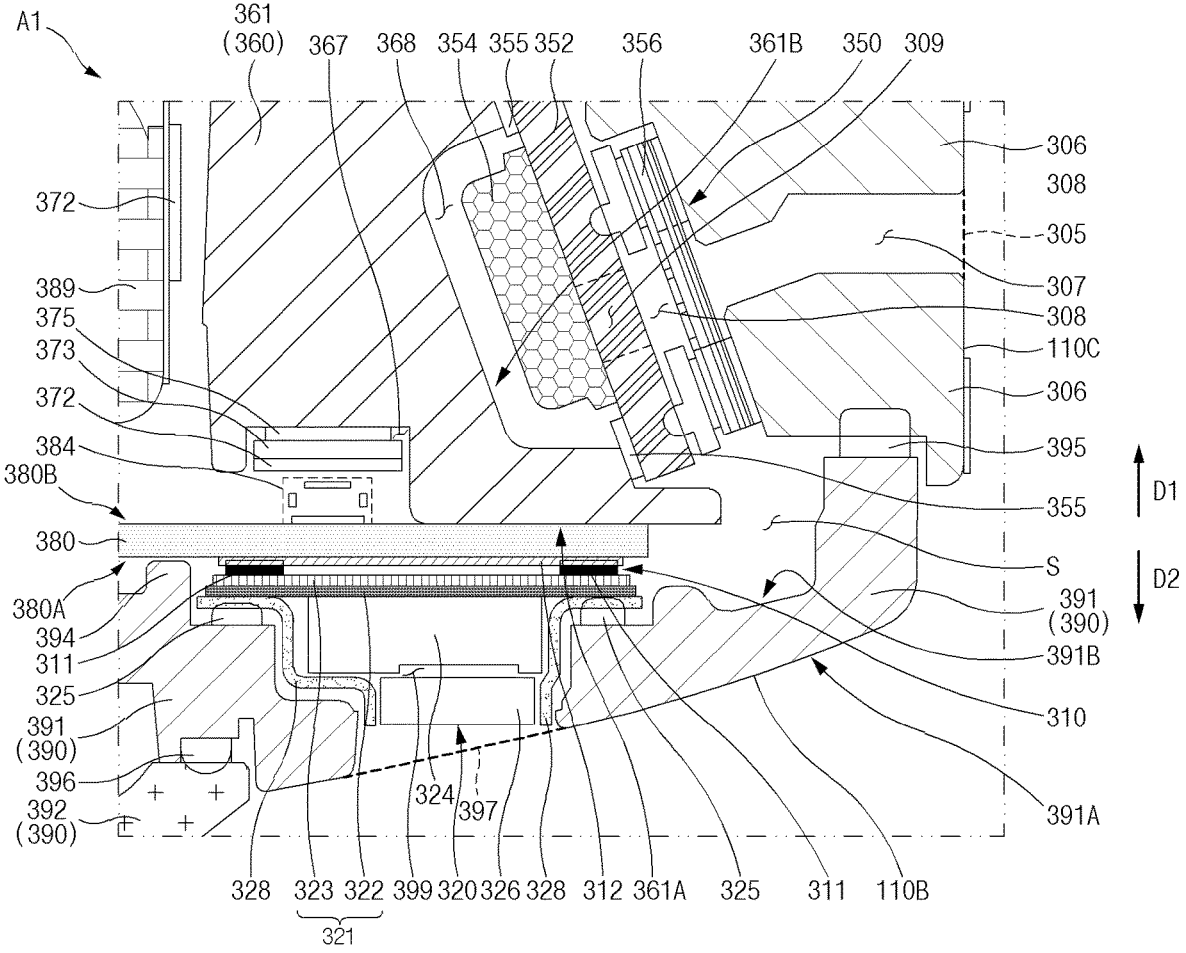
FIG. 5 is a cross-sectional view of a wearable electronic device according to an embodiment of the disclosure.

FIG. 5 is a cross-sectional view of a wearable electronic device according to an embodiment of the disclosure. FIG. 5 may be a view illustrating an area A1 of FIG. 4.

Referring to FIGS. 4 and 5, the wearable electronic device 300 according to an embodiment may include capacitors 382 disposed on the printed circuit board 380, and a connector 384. The capacitors 382, for example, may have a capacity of 1.0 μF, but the disclosure is not limited thereto. The capacitor having a capacity of 1.0 μF may be referred to as a high-capacity capacitor. The capacitors 382 may be disposed on a first surface 380A and/or a second surface 380B of the printed circuit board 380. The first surface 380A and the second surface 380B of the printed circuit board 380 may be opposite to each other. For example, the first surface 380A of the printed circuit board 380 may face the rear cover 390 (or the second direction D2). The second surface 380B of the printed circuit board 380 may face the front cover 101 (or the first direction D1).

The wearable electronic device 300 according to an embodiment may include a sealing member 395 disposed between the frame 306 and the first cover 391 and a sealing member 396 disposed between the first cover 391 and the second cover 392. The sealing member 395 may prevent introduction of foreign substances by sealing a gap between the frame 306 and the first cover 391. The sealing member 396 may prevent introduction of foreign substances by sealing a gap between the first cover 391 and the second cover 392.

The first sensor module 111 may be disposed in the rear cover 390. For example, the first sensor module 111 may be at least partially located in an interior of a hollow of the first cover 391. The first sensor module 111 may be disposed to face the second cover 392.

The first sensor module 111 may acquire biometric information through the second cover 392. For example, the first sensor module 111 may include a photoplethysmogram (PPG) sensor. The first sensor module 111 may acquire information on a heart rate or a blood oxygen saturation of a user by using the PPG sensor. However, the disclosure is not limited to the above-described example.

The bracket 360 may include a first part 361. The first part 361 may be located between the display 120 and the printed circuit board 380 with respect to the first direction D1. The first part 361 may be located between the front cover 101 and the biometric sensor structure 320 with respect to the first direction D1. The first part 361 may at least partially overlap the biometric sensor structure 320 with respect to the first direction D1. The first part 361 may be located between the battery 389 and the frame 306 with respect to the first direction D1.

The first part 361 of the bracket 360 may include a first surface 361A and the second surface 361B. The first surface 361A may at least partially face the printed circuit board 380. For example, the first surface 361A of the first part 361 may face the second surface 380B of the printed circuit board 380. The first surface 361A may at least partially contact the second surface 380B of the printed circuit board 380, but the disclosure is not limited thereto. The first surface 361A may at least partially overlap the biometric sensor structure 320 with respect to the first direction D1. A first recess 367 may be formed on the first surface 361A. The first recess 367 may be recessed on the first surface 361A of the first part 361 in a direction (e.g., the first direction D1) that becomes farther away from the printed circuit board 380.

The wearable electronic device 300 according to an embodiment may include a connection member 372 located in the first recess 367, a support plate 373, a bonding member 375, and the connector 384. The connection member 372 may electrically connect the battery 389 to the connector 384 disposed on the second surface 380B of the printed circuit board 380. The connection member 372, for example, may include a flexible printed circuit board. The connection member 372 may be disposed on the support plate 373 to be supported. The support plate 373 may reinforce a strength of the connection member 372 and prevent deformation thereof. The support plate 373, for example, may include a complex material including a glass fiber, such as flame retardant 4 (FR4), and an epoxy resin, but the disclosure is not limited thereto. The bonding member 375 may attach the support plate 373, in which the connection member 372 is disposed, to the first recess 367. The bonding member 375, for example, may include a double-sided tape. The connector 384, for example, may include a C-clip connector, but the disclosure is not limited thereto.

The second surface 361B of the first part 361 may face the frame 306. The second surface 361B may not contact the printed circuit board 380. A second recess 368 may be formed on the second surface 361B. The second recess 368 may be recessed on the second surface 361B in a direction that becomes farther away from the frame 306. For example, the second recess 368 may be recessed from the side surface 110C of the frame 306 in a direction that faces the interior space "S". The second surface 361B may extend from the first surface 361A, but the disclosure is not limited thereto.

The sound sensor structure 350 may be disposed on the second surface 361B of the first part 361. The sound sensor structure 350 may be at least partially accommodated in the second recess 368 formed on the second surface 361B. The sound sensor structure 350 may include a board 352, a sound sensor 354, and an acoustic gasket 356.

The board 352 of the sound sensor structure 350 may be disposed on the second surface 361B to at least partially cover the second recess 368. For example, the board 352 may be attached to the second surface 361B through a bonding member 355 that at least partially surrounds a periphery of the second recess 368. The board 352 may include the printed circuit board 380. The bonding member 355 may include a waterproof bonding tape, but the disclosure is not limited thereto.

The sound sensor 354 may be disposed on the board 352. For example, the sound sensor 354 may be disposed on one surface of the board 352 that faces the second recess 368. The sound sensor 354 may be at least partially located in the second recess 368. The sound sensor 354, for example, may include a microphone, such as a microelectromechanical systems (MEMS) microphone, and a sensing circuit that is operatively connected to the microphone.

The acoustic gasket 356 may be disposed on the board 352. For example, the sound gasket 356 may be disposed on an opposite surface to the one surface of the board 352, on which the sound sensor 354 is disposed. The acoustic gasket 356 may be disposed between the board 352 and the frame.

The wearable electronic device 300 according to an embodiment may include an acoustic channel of the sound sensor structure 350. The acoustic channel may include a first acoustic passage 307, a second acoustic passage 308, and an acoustic port 309. The first acoustic passage 307 may be formed to pass through the frame 306. The first acoustic passage 307 may extend from the microphone hole 305 formed on the side surface 110C to the acoustic gasket 356. The second acoustic passage 308 formed in the acoustic gasket 356 may extend from the frame 306 to the board 352. The second acoustic passage 308 may communicate the first acoustic port 307 of the frame 306 and the acoustic port 309 of the board 352. The acoustic port 309 may be formed in the board 352 to be connected to an acoustic sensor 354. The acoustic gasket 356, for example, may include silicon rubber to seal the acoustic channel, but the disclosure is not limited thereto. The acoustic gasket 356 also may include a mesh that prevents deformation of the acoustic gasket 356 itself or a material that constitutes the acoustic gasket 356, porous materials, and/or a membrane that delivers a sound (quiver of air) introduced into the first acoustic passage 307 to the second acoustic passage 308. The acoustic sensor 354 may acquire a sound signal that is delivered to the second acoustic passage 308 after passing through the first acoustic passage 307, through the acoustic channel. However, unlike the illustration, the first acoustic passage 307 may be formed in the first cover 391 (e.g., a first acoustic passage 607 of FIG. 7). In this case, the sound sensor structure 350 may be installed in the bracket 360 of the rear cover 391. Furthermore, the acoustic gasket 356 may be disposed between the board 352 and the first cover 391.

The first cover 391 of the rear cover 390 may include a first surface 391A and a second surface 391B. The first surface 391A may at least partially define the rear surface 110B. The second surface 391B that is opposite to the first surface 391A may face the printed circuit board 380. A through-hole 399 may be formed in the first cover 391. The through-hole 399 may extend from the first surface 391A to the second surface 391B. The through-hole 399 may have different diameters, but the disclosure is not limited thereto.

The biometric sensor structure 320 may be installed in the rear cover 390. For example, the biometric sensor structure 320 may be disposed in the first cover 391. For example, the biometric sensor structure 320 may be at least partially accommodated in the through-hole 399 of the first cover 391. The biometric sensor structure 320 may acquire biometric information through an opening 397 of the first cover 391. The biometric information acquired by the biometric sensor structure 320 may be different from that of the first sensor module 111. The biometric sensor structure 320 may include a biometric sensor 324, a lens 326, a sensor housing 328, a board 322, and a support plate 323. The board 322 and support plate 323 for a structure 321 to which the sensor housing 328 is attached.

The biometric sensor 324 may be disposed on the board 322. For example, the biometric sensor 324 may be disposed on one surface of the board 322 that faces the opening 397 of the first cover 391. The biometric sensor 324 may be at least partially located in the through-hole 399 of the first cover 391. The biometric sensor 324 may be disposed in the sensor housing 328 disposed in the board 322. The biometric sensor 324 may be located between the board 322 and the lens 326.

The lens 326 may be coupled to the sensor housing 328. The lens 326 may be located between the biometric sensor 324 and the opening 397. The lens 326 may be configured to transmit light of a specific wavelength band. For example, the lens 326 may include a silicon lens or a glass lens that may transmit light of a long wave infrared (LWIR) band, but the disclosure is not limited to the above-described example.

The biometric sensor 324, the lens 326, and the opening 397 may be at least partially aligned. For example, the biometric sensor 324, the lens 326, and the opening 397 may be at least partially aligned with respect to one direction (e.g., the second direction D2).

The biometric sensor may detect biometric information of the user through the lens 326. For example, the biometric sensor 324 may include a temperature sensor (e.g., an optical temperature sensor). The biometric sensor 324, for example, may detect a body temperature of the user by using the temperature sensor. However, the disclosure is not limited to the above-described example.

The support plate 323 of the biometric sensor structure 320 may be disposed on the board 322. For example, the support plate 323 may be disposed on an opposite surface to the one surface of the board 322, on which the biometric sensor 324 is disposed. The support plate 323 may be disposed between the board 322 and the damping structure 310. The support plate 323 may support the board 322. The support plate 323 may reinforce a strength of the board 322 and prevent deformation thereof. The support plate 323, for example, may include a metal, such as stainless steel, but the disclosure is not limited thereto.

In an embodiment of the disclosure, the sensor housing 328 may be disposed on the board 322. For example, the sensor housing 328 may be disposed on the one surface of the board 322, on which the biometric sensor 324 is disposed. The sensor housing 328 may at least partially surround the biometric sensor 324 and the lens 326. The sensor housing 328 may protect the biometric sensor 324 and the lens 326, which are disposed in an interior thereof. The sensor housing 328 may include a metal, but the disclosure is not limited thereto.

The sensor housing 328 may have a shape that is substantially similar to the through-hole 399. A bonding member 325 may be interposed between the sensor housing 328 and the first cover 391. For example, the bonding member 325 may be disposed between the sensor housing 328 and the through-hole 399. The bonding member 325 may be at least partially filled in a gap between the sensor housing 328 and the through-hole 399. The bonding member 325 may prevent foreign substances (e.g., moisture or dust) from being introduced between the sensor housing 328 and the through-hole 399 while bonding the biometric sensor structure 320 to the first cover 391. The bonding member 325, for example, may be formed by applying and curing a bonding liquid, but the disclosure is not limited thereto.

The damping structure 310 may be interposed between the printed circuit board 380 and the biometric sensor structure 320. For example, the damping structure 310 may be disposed between the first surface 380A of the printed circuit board 380 and the support plate 323 of the biometric sensor structure 320.

The damping structure 310 may be located between the capacitors 382 and the sound sensor 354 with respect to a direction (a direction that is perpendicular to the first direction D1) that is parallel to the first surface 380A or the second surface 380B of the printed circuit board 380. The printed circuit board 380 may include a side portion that is closer to the sound sensor structure 350, and the damping structure 310 may contact the side portion of the printed circuit board 380. No capacitor may be disposed on the first surface 380A and the second surface 380B of the printed circuit 380, between the damping structure 310 and the sound sensor 354, but The damping structure 310 may elastically support the printed circuit board 380 and the biometric sensor structure 320. For example, the damping structure 310 may include the first member 311 and the second member 312 having repulsive forces of specific values. The repulsion indexes of the first member 311 and the second member 312 may be different. The repulsion index (25% C.F.D (compression force deflection) of the first member 311, for example, may be 0.3 kgf/cm² to 3.0 kgf/cm². However, the repulsion index (25% C.F.D) of the first member 311 may be realized by using a material of a very low repulsive force of 0.3 kgf/cm² or less. The repulsion index of the second member 312 may be larger than the repulsion index of the first member 311. However, the repulsion index (25% C.F.D) of the second member 312 may be 3 kgf/cm² or less. The first member 311, for example, may include sponge. The sponge, for example, may include urethane, silicon, or rubber, but the disclosure is not limited thereto. The second member 312, for example, may include polyethylene terephthalate (PET). The second member 312 may have a film form, but the disclosure is not limited thereto.

Although not illustrated, the damping structure 310 may include at least two of a first bonding layer, a second bonding layer, and a third bonding layer. The first bonding layer may be disposed between the biometric sensor structure 320 and the first member 311. The first bonding layer may attach the first member 311 to the support plate 323 of the biometric sensor structure 320. The second bonding layer may be disposed between the first member 311 and the second member 312. The second bonding layer may bond the first member 311 and the second member 312. The third member 312 may be disposed between the second member 312 and the printed circuit board 380. The third bonding layer may attach the second member 312 to the first surface 380A of the printed circuit board 380. As an example, the damping structure 310 may include the first bonding layer and the third bonding layer, and may include no second bonding layer. In this case, while the printed circuit board 380, to which the second member 312 is attached, and the biometric sensor structure 320, to which the first member 311 is attached, is assembled, the second member 312 may be stacked on the first member 311 with no separate member.

The capacitors mounted on the printed circuit board 380 may vibrate while being repeatedly expanded and contracted by an applied voltage. The vibrations of the capacitors 382 may be delivered to the printed circuit board 380. The vibrations delivered to the printed circuit board 380 are noise, and may be heard by the user or be delivered to the sound sensor 354. Furthermore, the wearable electronic device having a relatively small volume and a narrow interior space may be more vulnerable to vibrations and noise because the printed circuit board 380 and the sound sensor 354 are disposed to be closer to each other.

The damping structure 310 may elastically support the printed circuit board 380 in a direction (e.g., the first direction D1) that is perpendicular to the printed circuit board 380. The damping structure 310 may damp the vibrations that are caused by the capacitors 382 and delivered to the printed circuit board 380, and may restrain and/or prevent the vibrations due to the capacitors 382 from being delivered to the sound sensor 354 as audible noise.

The damping structure 310 may provide repulsive forces (or damping forces) of different magnitudes to the printed circuit board 380 and the biometric sensor structure 320. For example, the repulsive forces of the damping structure 310 in the first direction D1 and the second direction D2 may be different. For example, in the repulsive force provided in the first direction D1 by the damping structure 310, the repulsive force by the second member 312 that contacts the printed circuit board 380 may be dominant, and in the repulsive force provided in the second direction D2, the repulsive force by the first member 311 that contacts the biometric sensor structure 320 may be dominant. Because the repulsion index of the second member 312 is larger than the repulsion index (or hardness) of the first member 311, the repulsive force provided in the first direction D1 by the damping structure 310 may be higher than that in the second direction. When the repulsive force in the second direction D2 is higher than necessary, the biometric sensor structure 320 may be moved in the first direction D1 or the second direction D2, and this may badly influence a performance of the biometric sensor 324. Furthermore, when the repulsive force in the second direction D2 is higher than necessary, a waterproof performance between the biometric sensor structure 320 and the first cover 391, which is provided by the bonding member 325, may be degraded. When the repulsive force in the first direction D1 is lower than required, it may be difficult to damp the vibrations delivered to the printed circuit board 380. The damping structure 310 may minimize an influence on the biometric sensor structure 320 while damping the vibrations delivered to the printed circuit board 380 by providing the repulsive forces of the different magnitudes in the first direction D1 and the second direction D2.

The first cover 391, for example, may include a protrusion 394. The protrusion 394 may protrude from the second surface 391B toward the printed circuit board 380. The protrusion 394 may at least partially overlap the biometric sensor structure 320 with respect to a direction that is perpendicular to the first direction D1. Additionally, although not illustrated, a damping structure including the first member 311 and/or the second member 312 may be disposed between the protrusion 394 and the first surface 380A of the printed circuit board 380. Additionally, although not illustrated, a damping structure including the first member 311 and/or the second member 312 may be disposed in an area, in which the first surface 361A of the bracket 360 and the second surface 380B of the printed circuit board 380 contact each other. The first member 311 and the second member 312 of the damping structure 310 may be exchanged.

According to the models of the produced products, a distance between the biometric sensor structure 320 and the printed circuit board 380 may be different. For example, the distance between the biometric sensor structure 320 and the printed circuit board 380 may become larger than illustrated (however, absolutes or relative sizes of the illustrated configurations are not limited by the illustrated example). In this case, in the damping structure 310, a thickness of the first member 311 and/or the second member 312 may further become larger to compensate for the increased distance between the printed circuit board 380 and the biometric sensor structure 320. Alternatively, the damping structure 310 may further include a third member stacked on the first member 311 or the second member 312 to compensate for the increased distance between the printed circuit board 380 and the biometric sensor structure 320. The third member may be substantially the same as the first member 311 and the second member 312. On the contrary, the distance between the biometric sensor structure 320 and the printed circuit board 380 may become smaller than illustrated. In this case, the thickness of the first member 311 and/or the second member 312 may become smaller to compensate for the decreased distance between the printed circuit board 380 and the biometric sensor structure 320. Alternatively or additionally, the damping structure 310 may include no second member 312 to compensate for the decreased distance between the printed circuit board 380 and the biometric sensor structure 320.

The wearable electronic device 100 and 300 according to an embodiment may include the housing 110 including the cover 390. The wearable electronic device 100 and 300 may include the bracket 360 that is disposed in the housing 110 and includes the first part 361. The wearable electronic device 100 and 300 may include the printed circuit board 380 that is disposed between the cover 390 and the bracket 360 and at least partially faces the first surface 361A of the first part 361 of the bracket 360. The wearable electronic device 100 and 300 may include the sound sensor structure 350 that is disposed on the second surface 361B that is different from the first surface 361A of the first part 361 of the bracket 360. The wearable electronic device 100 and 300 may include the biometric sensor structure 320 that is installed in the cover 390 to overlap the first surface 361Aa of the first part 361 of the bracket 360 with respect to the direction D1 that is perpendicular to the printed circuit board 380. The wearable electronic device 100 and 300 may include the damping structure 310 that is interposed between the biometric sensor structure 320 and the printed circuit board 380 and elastically supports the biometric sensor structure 320 and the printed circuit board 380. The damping structure 310 may reduce or eliminate the noise due to the vibrations of the printed circuit board 380 by damping the vibrations.

In an embodiment of the disclosure, the damping structure 310 may include the first member 311 having a repulsive force of a specific value.

In an embodiment of the disclosure, the damping structure 310 may include the second member 312 that is stacked on the first member 311, and the repulsive force of the first member may be different from the repulsive force of the second member.

In an embodiment of the disclosure, the first member 311 may be disposed between the biometric sensor structure 320 and the second member 312, and the second member 312 may be disposed between the first member 311 and the printed circuit board 380.

In an embodiment of the disclosure, the repulsive force of the first member 311 may be lower than the repulsive force of the second member 312.

In an embodiment of the disclosure, the first member 311 may include sponge.

In an embodiment of the disclosure, the second member 312 may include a polyethylene terephthalate (PET) film.

In an embodiment of the disclosure, the printed circuit board 380 may include the first surface 380A that faces the cover 390, and the second surface 380B that faces the first surface 380A. The biometric sensor structure 320 may include the board 322 that is disposed above the first surface 380A of the printed circuit board 380, and the temperature sensor 324 that is disposed on the board 322 to face the cover 390. The first member 311 may be disposed between the board 322 and the second member 312. The second member 312 may be disposed between the first surface 380A of the printed circuit board 380 and the first member 311.

In an embodiment of the disclosure, the damping structure 310 may include at least two of the first bonding layer, the second bonding layer, and the third bonding layer. The first bonding layer may be disposed between the biometric sensor structure 320 and the first member 311. The second bonding layer may be disposed between the first member 311 and the second member 312. The third member 312 may be disposed between the second member 312 and the printed circuit board 380.

In an embodiment of the disclosure, the first member 311 may have a hollow.

The wearable electronic device 100 and 300 according to an embodiment may include the battery 389 that is at least partially accommodated in an interior of the bracket 360, and the connection member 372 that electrically connects the battery 389 and the printed circuit board 380. The housing 110 may include the frame 306, to which the cover 390 is coupled. The first part 361 of the bracket 360 may be located between the battery 389 and the frame 306. The first recess 367, in which the connection member 372 is disposed, may be formed on the first surface 361A of the first part 361 of the bracket 360. The second recess 368, in which the sound sensor structure 350 is at least partially accommodated, may be formed on the second surface 361B of the first part 361 of the bracket 360.

The wearable electronic device 100 and 300 according to an embodiment may include the sensor module 111. The cover 390 may include the first cover 391, and the second cover 392 coupled to the first cover 391 to close the hollow formed in the first cover 391. The biometric sensor structure 320 may be at least partially accommodated in the through-hole 399 formed in the first cover 391. The sensor module 111 may be disposed on a rear surface of the second cover 392. The biometric sensor structure 320 may be configured to detect first biometric information including a temperature of the body of the user, which contacts the cover 390, through the through-hole 399. The sensor module 111 may be configured to detect biometric information that is different from the first biometric information.

The wearable electronic device 100 and 300 according to an embodiment may include a second damping structure and/or a third damping structure. The cover 390 may include the protrusion 394 that extends toward the printed circuit board 380. The protrusion 394 may at least partially overlap the biometric sensor structure 320 with respect to a direction that is parallel to the printed circuit board 380. The second damping structure may be disposed between the protrusion 394 and the printed circuit board 380. The second damping structure may elastically support the printed circuit board 380. The third damping structure may be disposed between the printed circuit board 380, and the first surface 361A of the first part 361 of the bracket 360. The third damping structure may elastically support the printed circuit board 380.

The wearable electronic device 100 and 300 according to an embodiment may include the capacitor 382 disposed in the printed circuit board 380. The damping structure 310 may be located between the sound sensor structure 350 and the capacitor 382, with respect to a direction that is parallel to the printed circuit board 380.

In an embodiment of the disclosure, the printed circuit board 380 may include a part between the damping structure 310 and the sound sensor structure 350 with respect to a direction that is parallel to the printed circuit board 380. No capacitor may be disposed in the part of the printed circuit board 380.

Figure 6:
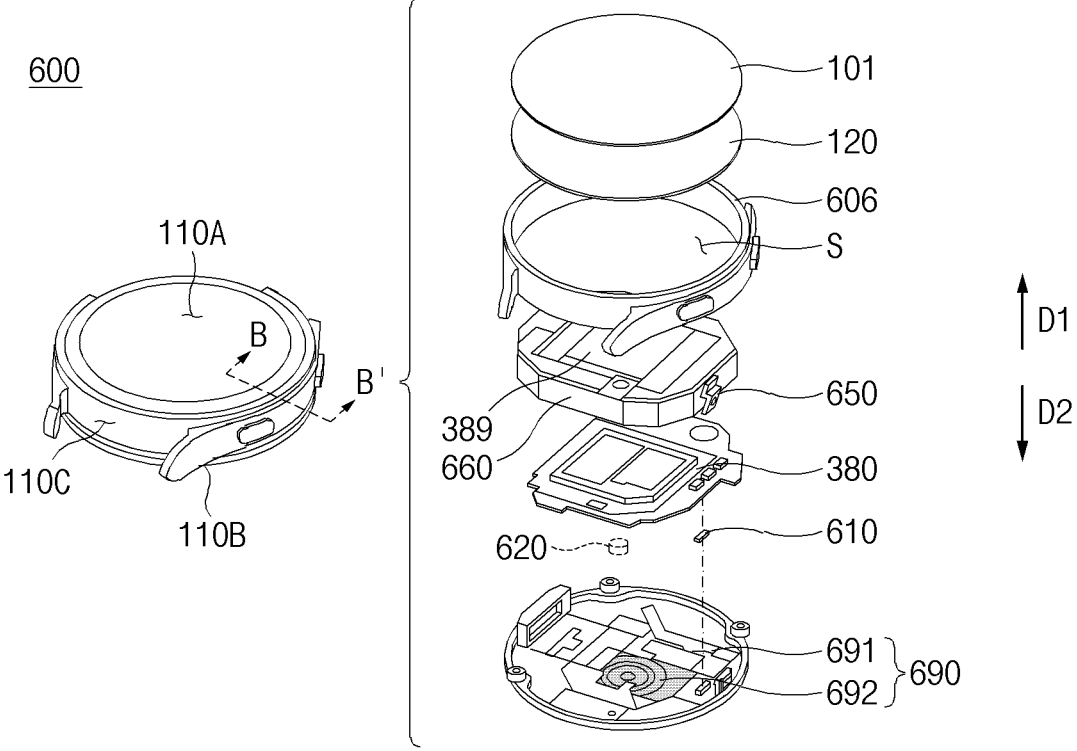
FIG. 6 is an exploded perspective view of a wearable electronic device according to an embodiment of the disclosure.

FIG. 6 is an exploded perspective view of a wearable electronic device according to an embodiment of the disclosure.

Referring to FIG. 6, a wearable electronic device 600 (e.g., the wearable electronic device 100 of FIG. 1) according to an embodiment may include a rear cover 690, a frame 606, a bracket 660, a sound sensor structure 650, a biometric sensor structure 620, and a damping structure 610.

For the rear cover 690, the frame 606, the bracket 660, the sound sensor structure 650, the biometric sensor structure 620, and the damping structure 610 of the wearable electronic device 600, the description of the rear cover 390, the frame 306, the bracket 360, the sound sensor structure 350, the biometric sensor structure 320, and the damping structure 310 of the wearable electronic device 300, which has been made with reference to FIGS. 3, 4, and 5, may be applied in substantially the same way, similarly, or in a corresponding scheme. For example, the damping structure 610 may include the first member 311, and may further include the second member 312. Hereinafter, a repeated description thereof may be omitted.

The rear cover 690 may include a first cover 691 and a second cover 692. The biometric sensor structure 620 may be installed in the rear cover 690. For example, the biometric sensor structure 620 may be installed in the second cover 692 of the rear cover 690, but the disclosure is not limited thereto. For example, the biometric sensor structure 620 may be installed in the first cover 611. The biometric sensor structure 620 may not overlap the damping structure 610 with respect to the second direction D2. The damping structure 610 may be disposed between the printed circuit board 380 and the rear cover 690. Selectively, the wearable electronic device 600 according to an embodiment may include no biometric sensor structure 620.

Figure 7:
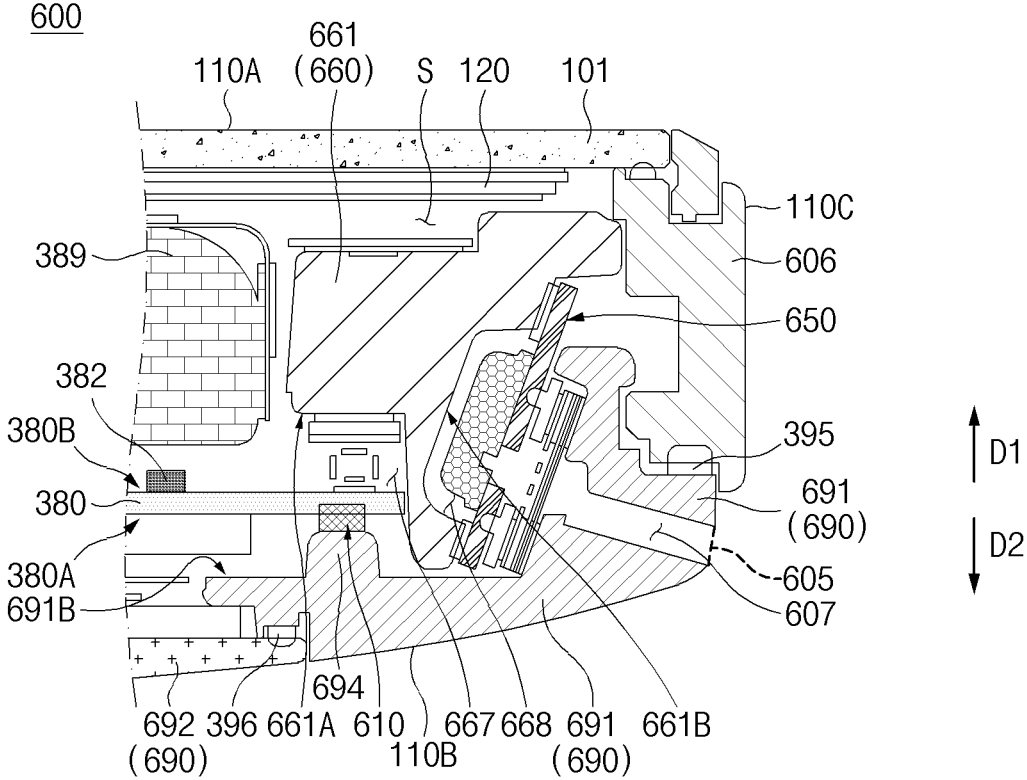
FIG. 7 is a cross-sectional view of a wearable electronic device according to an embodiment of the disclosure.

FIG. 7 is a cross-sectional view of a wearable electronic device according to an embodiment of the disclosure. FIG. 7 may be a cross-sectional view taken along line B-B' of FIG. 6.

Referring to FIG. 7, the bracket 660 may include a first part 661. The first part 661 may include a part located between the display 120 and the printed circuit board 380 with respect to the first direction D1. The first part 661 may be located between the front cover 101 and the first cover 691 of the cover 690 with respect to the first direction D1. The first part 661 may at least partially overlap the damping structure 610 and a protrusion 694, in which the damping structure 610 is disposed, with respect to the first direction D1. The first part 661 may be located between the battery 389 and the frame 606 with respect to the first direction D1.

The first part 661 of the bracket 660 may include a first surface 661A and a second surface 661B. The first surface 661A of the first part 661 may at least partially face the printed circuit board 380. For example, the first surface 661A may include a first area (e.g., an area that faces the second direction D2) that faces the second surface 380B of the printed circuit board 380, and a second area that extends from the first area toward the first cover 691. The second area of the first surface 661A may face the printed circuit board 380 in a direction that is perpendicular to the first direction D1. The first surface 661A may at least partially contact the printed circuit board 380, but the disclosure is not limited thereto. For example, the first surface 661A may at least partially contact a side surface (e.g., a side surface between the first surface 380A and the second surface 380B) of the printed circuit board 380, but the disclosure is not limited thereto.

A first recess 667 may be formed on the first surface 661A. The first recess 667 may be recessed in a direction (e.g., the first direction D1) that becomes farther away from the printed circuit board 380. For example, the connection member 372, the support plate 373, the bonding member 375, and the connector 384 of FIG. 5 may be disposed in the first recess 667.

The second surface 661B of the first part 661 may face the frame 606. The second surface 661B may not contact the printed circuit board 380. The second surface 661B may face an opposite direction to the printed circuit board 380. A second recess 668 may be formed on the second surface 661B. The second recess 668 may be recessed on the second surface 661B in a direction that becomes farther away from the frame 606. For example, the second recess 668 may be recessed from the side surface 110C of the frame 606 in a direction that faces the interior space "S". The second surface 661B may extend from the first surface 661A, but the disclosure is not limited thereto.

The sound sensor structure 650 may be disposed on the second surface 661B of the first part 661. The sound sensor structure 650 may be at least partially accommodated in the second recess 668 formed on the second surface 661B. The sound sensor structure 650 may be disposed between the first part 661 of the bracket 660 and the first cover 691. The sound sensor structure 650 may be disposed on the second surface 661B of the bracket 660 to face the first acoustic passage 607 formed in the first cover 691. The first acoustic passage 607 may extend from a microphone hole 605 formed on a first surface 691A of a first cover 691 to the sound sensor structure 650. The first acoustic passage 607 may define the acoustic channel of the sound sensor structure 650. The sound sensor structure 650 may include the board 352, the sound sensor 354, and the acoustic gasket 356 of FIG. 5.

The first cover 691 of the rear cover 690 may include the first surface 691A and a second surface 691B. The first surface 691A may at least partially define the rear surface 110B. The second surface 691B that is opposite to the first surface 691A may face the printed circuit board 380.

The first cover 691 of the rear cover 690 may include the protrusion 694 formed on the second surface 691B. The protrusion 694 may protrude from the second surface 691B toward the printed circuit board 380. FIG. 7 illustrates that one protrusion 694 is provided, but the disclosure is not limited thereto. The protrusion 694 may protrude from one or a plurality of areas of the second surface 691B. For example, one or a plurality of protrusions 694 may be provided. In correspondence to the one or the plurality of protrusions 694, one or a plurality of damping structures 610 also may be provided. For example, one damping structure 610 may be provided in one protrusion 694. As another example, two damping structures 610 may be provided in two protrusions 694. As another example, two damping structures 610 may be provided in one protrusion 694.

The damping structure 610 may be disposed between the protrusion 694 and the first surface 380A of the printed circuit board 380. The damping structure 610 may contact the protrusion 694 and the first surface 380A of the printed circuit board 380. The damping structure 610 may be located between the capacitors 382 and the sound sensor 354 with respect to a direction (a direction that is perpendicular to the first direction D1) that is parallel to the first surface 380A or the second surface 380B of the printed circuit board 380. The printed circuit board 380 may include a side portion that is closer to the sound sensor structure 650, and the damping structure 610 may contact the side portion of the printed circuit board 380. No capacitor may be disposed on the first surface 380A and the second surface 380B of the printed circuit board 380, between the damping structure 610 and the sound sensor 354, but The damping structure 610 may elastically support the printed circuit board 380.

Although not illustrated, the damping structure 610, additionally or selectively, may be disposed between the printed circuit board 380 and the bracket 660. For example, the damping structure 610 may be disposed between the printed circuit board 380 and the first part 661 of the bracket 660. The damping structure 610 may elastically support the printed circuit board 380 and the bracket 660. For example, the damping structure 610 may be disposed in the first recess 657, and may elastically support the printed circuit board 380 and the first surface 661A of the bracket 660. As another example, the damping structure 610 may be disposed between a side surface of the printed circuit board 380 and the first surface 661A of the bracket 660 that faces the side surface, and may elastically support the printed circuit board 380 and the bracket 660. However, a location, at which the damping structure 610 is disposed to elastically support the printed circuit board 380 and the bracket 660 is not limited to the above-described example, and various modifications may be made.

Although not illustrated, the damping structure 610 may include a first bonding layer and/or a second bonding layer. The first bonding layer may be disposed on the protrusion 694 to attach the damping structure 610 to the protrusion 694. The second bonding layer may be disposed on the first surface 380A of the printed circuit board 380 and may attach the damping structure 610 to the printed circuit board 380. As an example, the damping structure 610 may include the first bonding layer, and may include no second bonding layer. In this case, while the first cover 691, to which the damping structure 610 is attached, and the printed circuit board 380 are assembled, the damping structure 610 may be pressed and attached by the printed circuit board 380.

The damping structure 610 may elastically support the printed circuit board 380 in a direction (e.g., the first direction D1) that is perpendicular to the printed circuit board 380. The damping structure 610 may damp the vibrations that are caused by the capacitors 382 and delivered to the printed circuit board 380, and may restrain and/or prevent the vibrations due to the capacitors 382 from being delivered to the sound sensor 354 as audible noise.

Figure 8:
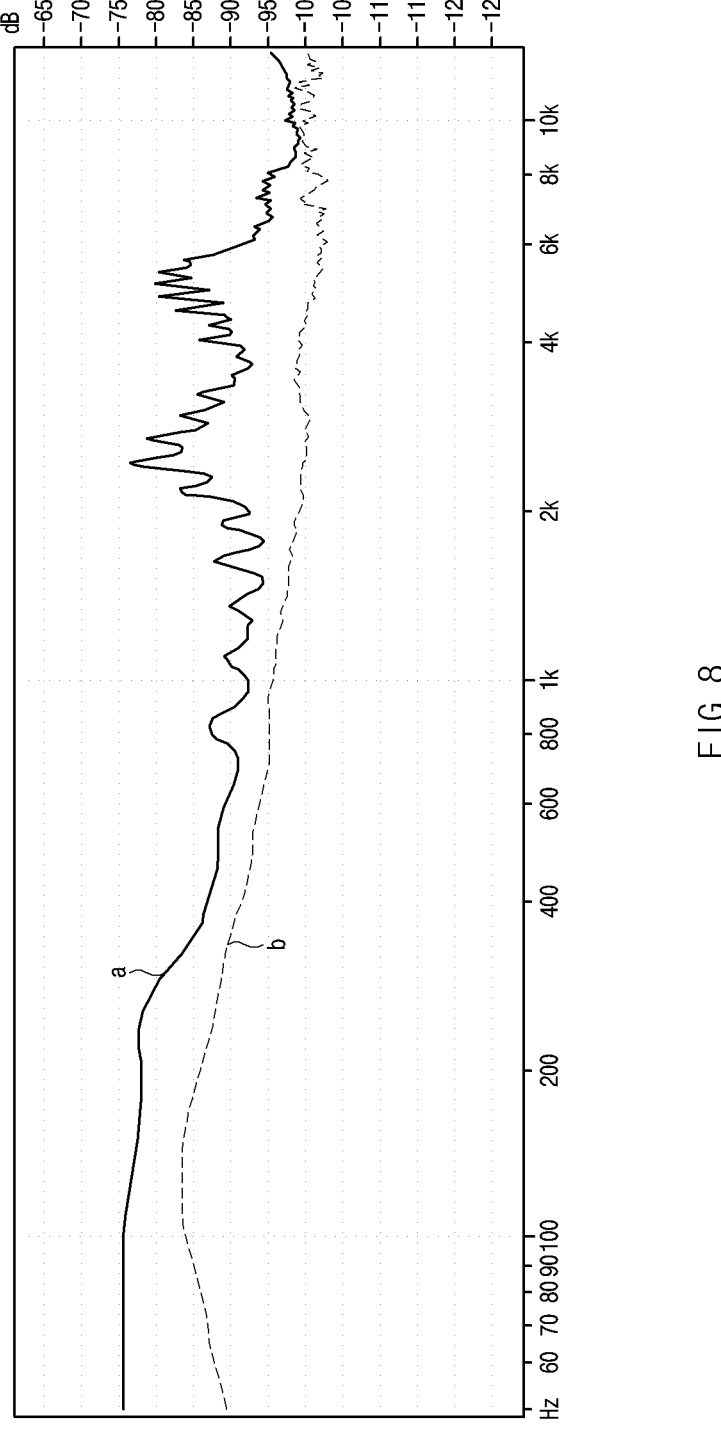
FIG. 8 is a graph depicting sound signals received by a sound sensor according to an embodiment of the disclosure.

FIG. 8 is a graph depicting sound signals received by the sound sensor according to an embodiment of the disclosure. Graph (a) of FIG. 8 depicts a sound signal of an electronic device including no damping structure. Graph (b) of FIG. 8 depicts a sound signal of the wearable electronic device including a damping structure (e.g., the damping structure 310 or 610) according to an embodiment. Referring to FIG. 8, audible sounds may be reduced at all frequency bands or a specific frequency band having strong noise by the damping structure.

The wearable electronic device 100 and 600 according to an embodiment may include the housing 110 including the cover 690. The wearable electronic device 100 and 600 may include the bracket 660 that is disposed in the housing 110 and includes the first part 661. The wearable electronic device 100 and 600 may include the printed circuit board 380 that is disposed between the cover 690 and the bracket 660 and at least partially faces the first surface 661A of the first part 661 of the bracket 660. The wearable electronic device 100 and 600 may include the sound sensor structure 650 that is disposed on the second surface 661B that is different from the first surface 661A of the first part 661 of the bracket 660. The wearable electronic device 100 and 600 may include the damping structure 610. The cover 690 may include the protrusion 694 that extends toward the printed circuit board 380. The damping structure 610 may be disposed between the printed circuit board 380 and the protrusion 694. The damping structure 610 may elastically support the printed circuit board 380. The damping structure 610 may reduce or eliminate the noise due to the vibrations of the printed circuit board 380 by damping the vibrations.

In an embodiment of the disclosure, the damping structure 610 may include the first member 311 having a repulsive force of a specific value.

In an embodiment of the disclosure, the damping structure 610 may include the second member 312 stacked on the first member 311. The repulsive force of the first member 311 may be different from the repulsive force of the second member 312.

In an embodiment of the disclosure, the first member 311 of the damping structure 610 may be disposed between the protrusion 694 and the second member 312. The second member 312 of the damping structure 610 may be disposed between the first member 311 and the printed circuit board 380.

In an embodiment of the disclosure, the repulsive force of the first member 311 may be lower than the repulsive force of the second member 312.

In an embodiment of the disclosure, the first member 311 of the damping structure 610 may include sponge.

In an embodiment of the disclosure, the second member 312 of the damping structure 610 may include a polyethylene terephthalate (PET) film.

In an embodiment of the disclosure, the wearable electronic device 100 and 600 according to an embodiment may include the biometric sensor structure 320. The damping structure 610 may not overlap the biometric sensor structure 320 with respect to a direction that is perpendicular to the printed circuit board 380.

In an embodiment of the disclosure, the damping structure 610 may include at least two of the first bonding layer, the second bonding layer, and the third bonding layer. The first bonding layer may be disposed between the protrusion 694 and the first member 311. The second bonding layer may be disposed between the first member 311 and the second member 312. The third member 312 may be disposed between the second member 312 and the printed circuit board 380.

In an embodiment of the disclosure, the first member 311 of the damping structure 610 may have a hollow.

The wearable electronic device 100 and 600 according to an embodiment may include the battery 389 that is at least partially accommodated in an interior of the bracket 660, and the connection member 372 that electrically connects the battery 389 and the printed circuit board 380. The housing 110 may include the frame 606, to which the cover 690 is coupled. The first part 661 of the bracket 660 may be located between the battery 389 and the frame 606. The first recess 667, in which the connection member 372 is disposed, may be formed on the first surface 661A of the first part 661 of the bracket 660. The second recess 668, in which the sound sensor structure 650 is at least partially accommodated, may be formed on the second surface 661B of the first part 661 of the bracket 660.

The wearable electronic device 100 and 600 according to an embodiment may include the sensor module 111. The cover 690 may include the first cover 691, and the second cover 692 coupled to the first cover 691 to close the hollow formed in the first cover 691. The biometric sensor structure 320 may be installed in the first cover 391. The sensor module 111 may be disposed on a rear surface of the second cover 692. The biometric sensor structure 320 may be configured to detect first biometric information including a temperature of the body of the user, which contacts the cover 390. The sensor module 111 may be configured to detect biometric information that is different from the first biometric information.

The wearable electronic device 100 and 600 according to an embodiment may include a second damping structure (e.g., the damping structure 610). The damping structure may be disposed between the printed circuit board 380 and the first part 661 of the bracket 660. The second damping structure may elastically support the printed circuit board 380.

In an embodiment of the disclosure, the second damping structure may be disposed in the first recess 667 of the bracket 660.

The wearable electronic device 100 and 600 according to an embodiment may include the capacitor 382 disposed in the printed circuit board 380. The damping structure 610 may be located between the sound sensor structure 650 and the capacitor 382, with respect to a direction that is parallel to the printed circuit board 380.

In an embodiment of the disclosure, the printed circuit board 380 may include a part between the damping structure 610 and the sound sensor structure 650 with respect to a direction that is parallel to the printed circuit board 380. No capacitor may be disposed in the part of the printed circuit board 380.

Figure 9:
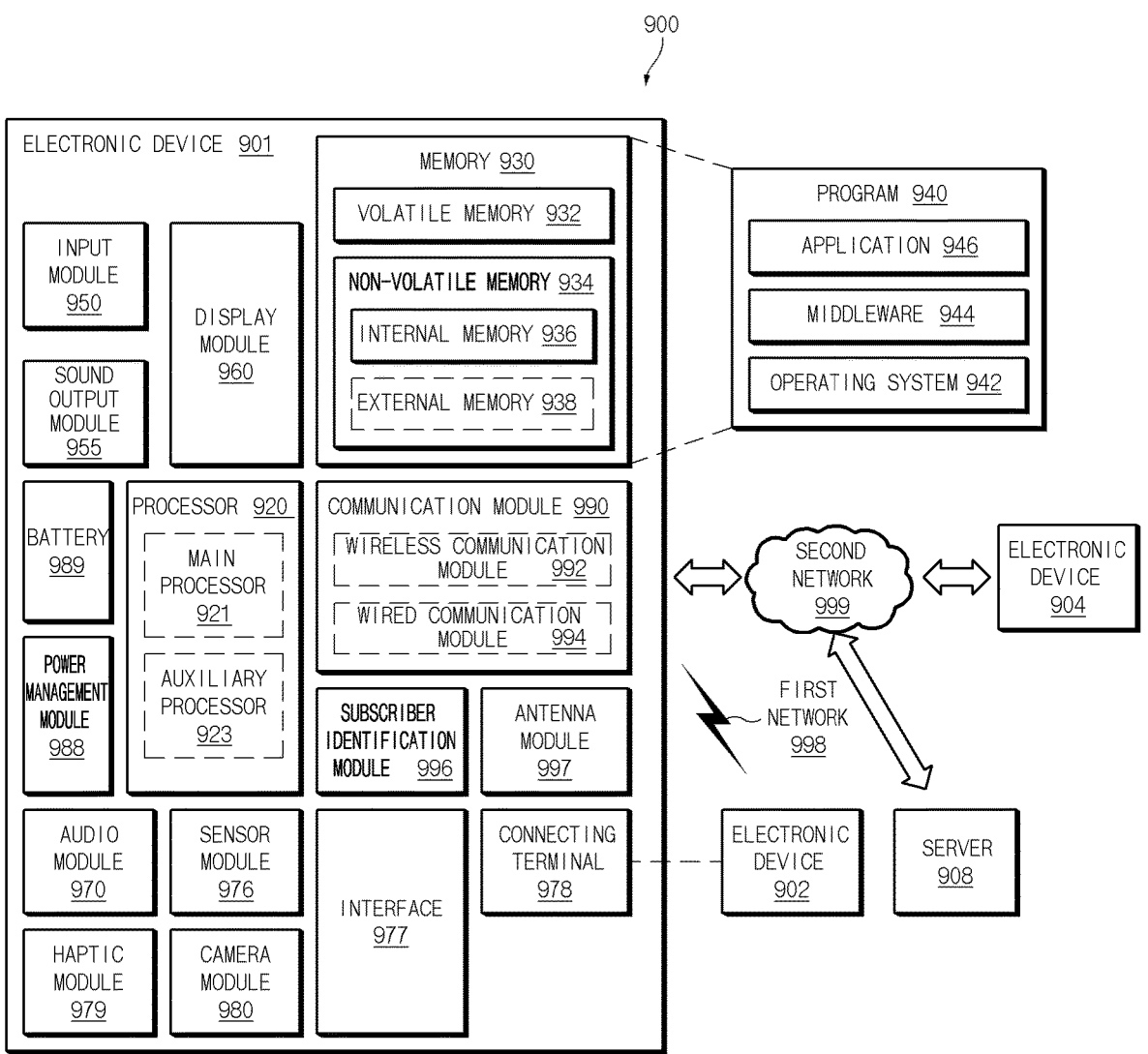
FIG. 9 is a block diagram of an electronic device in a network environment according to an embodiment of the disclosure.

FIG. 9 is a block diagram illustrating an electronic device 901 in a network environment 900 according to an embodiment of the disclosure.

Referring to FIG. 9, the electronic device 901 in the network environment 900 may communicate with an external electronic device 902 via a first network 998 (e.g., a short-range wireless communication network), or at least one of an external electronic device 904 or a server 908 via a second network 999 (e.g., a long-range wireless communication network). According to an embodiment of the disclosure, the electronic device 901 may communicate with the external electronic device 904 via the server 908. According to an embodiment of the disclosure, the electronic device 901 may include a processor 920, a memory 930, an input module 950, a sound output module 955, a display module 960, an audio module 970, a sensor module 976, an interface 977, a connecting terminal 978, a haptic module 979, a camera module 980, a power management module 988, a battery 989, a communication module 990, a subscriber identification module (SIM) 996, or an antenna module 997. In some embodiments of the disclosure, at least one of the components (e.g., the connecting terminal 978) may be omitted from the electronic device 901, or one or more other components may be added in the electronic device 901. In some embodiments of the disclosure, some of the components (e.g., the sensor module 976, the camera module 980, or the antenna module 997) may be implemented as a single component (e.g., the display module 960).

The processor 920 may execute, for example, software (e.g., a program 940) to control at least one other component (e.g., a hardware or software component) of the electronic device 901 coupled with the processor 920, and may perform various data processing or computation. According to one embodiment of the disclosure, as at least part of the data processing or computation, the processor 920 may store a command or data received from another component (e.g., the sensor module 976 or the communication module 990) in a volatile memory 932, process the command or the data stored in the volatile memory 932, and store resulting data in a non-volatile memory 934. According to an embodiment of the disclosure, the processor 920 may include a main processor 921 (e.g., a central processing unit (CPU) or an application processor (AP)), or an auxiliary processor 923 (e.g., a graphics processing unit (GPU), a neural processing unit (NPU), an image signal processor (ISP), a sensor hub processor, or a communication processor (CP)) that is operable independently from, or in conjunction with, the main processor 921. For example, when the electronic device 901 includes the main processor 921 and the auxiliary processor 923, the auxiliary processor 923 may be adapted to consume less power than the main processor 921, or to be specific to a specified function. The auxiliary processor 923 may be implemented as separate from, or as part of the main processor 921.

The auxiliary processor 923 may control at least some of functions or states related to at least one component (e.g., the display module 960, the sensor module 976, or the communication module 990) among the components of the electronic device 901, instead of the main processor 921 while the main processor 921 is in an inactive (e.g., sleep) state, or together with the main processor 921 while the main processor 921 is in an active state (e.g., executing an application). According to an embodiment of the disclosure, the auxiliary processor 923 (e.g., an image signal processor or a communication processor) may be implemented as part of another component (e.g., the camera module 980 or the communication module 990) functionally related to the auxiliary processor 923. According to an embodiment of the disclosure, the auxiliary processor 923 (e.g., the neural processing unit) may include a hardware structure specified for artificial intelligence model processing. An artificial intelligence model may be generated by machine learning. Such learning may be performed, e.g., by the electronic device 901 where the artificial intelligence is performed or via a separate server (e.g., the server 908). Learning algorithms may include, but are not limited to, e.g., supervised learning, unsupervised learning, semi-supervised learning, or reinforcement learning. The artificial intelligence model may include a plurality of artificial neural network layers. The artificial neural network may be a deep neural network (DNN), a convolutional neural network (CNN), a recurrent neural network (RNN), a restricted boltzmann machine (RBM), a deep belief network (DBN), a bidirectional recurrent deep neural network (BRDNN), deep Q-network or a combination of two or more thereof but is not limited thereto. The artificial intelligence model may, additionally or alternatively, include a software structure other than the hardware structure.

The memory 930 may store various data used by at least one component (e.g., the processor 920 or the sensor module 976) of the electronic device 901. The various data may include, for example, software (e.g., the program 940) and input data or output data for a command related thererto. The memory 930 may include the volatile memory 932 or the non-volatile memory 934.

The program 940 may be stored in the memory 930 as software, and may include, for example, an operating system (OS) 942, middleware 944, or an application 946.

The input module 950 may receive a command or data to be used by another component (e.g., the processor 920) of the electronic device 901, from the outside (e.g., a user) of the electronic device 901. The input module 950 may include, for example, a microphone, a mouse, a keyboard, a key (e.g., a button), or a digital pen (e.g., a stylus pen).

The sound output module 955 may output sound signals to the outside of the electronic device 901. The sound output module 955 may include, for example, a speaker or a receiver. The speaker may be used for general purposes, such as playing multimedia or playing record. The receiver may be used for receiving incoming calls. According to an embodiment of the disclosure, the receiver may be implemented as separate from, or as part of the speaker.

The display module 960 may visually provide information to the outside (e.g., a user) of the electronic device 901. The display module 960 may include, for example, a display, a hologram device, or a projector and control circuitry to control a corresponding one of the display, hologram device, and projector. According to an embodiment of the disclosure, the display module 960 may include a touch sensor adapted to detect a touch, or a pressure sensor adapted to measure the intensity of force incurred by the touch.

The audio module 970 may convert a sound into an electrical signal and vice versa. According to an embodiment of the disclosure, the audio module 970 may obtain the sound via the input module 950, or output the sound via the sound output module 955 or a headphone of an external electronic device (e.g., the external electronic device 902) directly (e.g., wiredly) or wirelessly coupled with the electronic device 901.

The sensor module 976 may detect an operational state (e.g., power or temperature) of the electronic device 901 or an environmental state (e.g., a state of a user) external to the electronic device 901, and then generate an electrical signal or data value corresponding to the detected state. According to an embodiment of the disclosure, the sensor module 976 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 977 may support one or more specified protocols to be used for the electronic device 901 to be coupled with the external electronic device (e.g., the external electronic device 902) directly (e.g., wiredly) or wirelessly. According to an embodiment of the disclosure, the interface 977 may include, for example, a high definition multimedia interface (HDMI), a universal serial bus (USB) interface, a secure digital (SD) card interface, or an audio interface.

The connecting terminal 978 may include a connector via which the electronic device 901 may be physically connected with the external electronic device (e.g., the external electronic device 902). According to an embodiment of the disclosure, the connecting terminal 978 may include, for example, a HDMI connector, a USB connector, a SD card connector, or an audio connector (e.g., a headphone connector).

The haptic module 979 may convert an electrical signal into a mechanical stimulus (e.g., a vibration or a movement) or electrical stimulus which may be recognized by a user via his tactile sensation or kinesthetic sensation. According to an embodiment of the disclosure, the haptic module 979 may include, for example, a motor, a piezoelectric element, or an electric stimulator.

The camera module 980 may capture a still image or moving images. According to an embodiment of the disclosure, the camera module 980 may include one or more lenses, image sensors, image signal processors, or flashes.

The power management module 988 may manage power supplied to the electronic device 901. According to one embodiment of the disclosure, the power management module 988 may be implemented as at least part of, for example, a power management integrated circuit (PMIC).

The battery 989 may supply power to at least one component of the electronic device 901. According to an embodiment of the disclosure, the battery 989 may include, for example, a primary cell which is not rechargeable, a secondary cell which is rechargeable, or a fuel cell.

The communication module 990 may support establishing a direct (e.g., wired) communication channel or a wireless communication channel between the electronic device 901 and the external electronic device (e.g., the external electronic device 902, the external electronic device 904, or the server 908) and performing communication via the established communication channel. The communication module 990 may include one or more communication processors that are operable independently from the processor 920 (e.g., the application processor (AP)) and supports a direct (e.g., wired) communication or a wireless communication. According to an embodiment of the disclosure, the communication module 990 may include a wireless communication module 992 (e.g., a cellular communication module, a short-range wireless communication module, or a global navigation satellite system (GNSS) communication module) or a wired communication module 994 (e.g., a local area network (LAN) communication module or a power line communication (PLC) module). A corresponding one of these communication modules may communicate with the external electronic device via the first network 998 (e.g., a short-range communication network, such as Bluetooth™, wireless-fidelity (Wi-Fi) direct, or infrared data association (IrDA)) or the second network 999 (e.g., a long-range communication network, such as a legacy cellular network, a fifth-generation (5G) network, a next-generation communication network, the Internet, or a computer network (e.g., local area network (LAN) or wide area network (WAN)). These various types of communication modules may be implemented as a single component (e.g., a single chip), or may be implemented as multi components (e.g., multi chips) separate from each other. The wireless communication module 992 may identify and authenticate the electronic device 901 in a communication network, such as the first network 998 or the second network 999, using subscriber information (e.g., international mobile subscriber identity (IMSI)) stored in the subscriber identification module 996.

The wireless communication module 992 may support a 5G network, after a fourth-generation (4G) network, and next-generation communication technology, e.g., new radio (NR) access technology. The NR access technology may support enhanced mobile broadband (eMBB), massive machine type communications (mMTC), or ultra-reliable and low-latency communications (URLLC). The wireless communication module 992 may support a high-frequency band (e.g., the mmWave band) to achieve, e.g., a high data transmission rate. The wireless communication module 992 may support various technologies for securing performance on a high-frequency band, such as, e.g., beamforming, massive multiple-input and multiple-output (massive MIMO), full dimensional MIMO (FD-MIMO), array antenna, analog beam-forming, or large scale antenna. The wireless communication module 992 may support various requirements specified in the electronic device 901, an external electronic device (e.g., the external electronic device 904), or a network system (e.g., the second network 999). According to an embodiment of the disclosure, the wireless communication module 992 may support a peak data rate (e.g., 20 Gbps or more) for implementing eMBB, loss coverage (e.g., 164 dB or less) for implementing mMTC, or U-plane latency (e.g., 0.5 ms or less for each of downlink (DL) and uplink (UL), or a round trip of 1 ms or less) for implementing URLLC.

The antenna module 997 may transmit or receive a signal or power to or from the outside (e.g., the external electronic device) of the electronic device 901. According to an embodiment of the disclosure, the antenna module 997 may include an antenna including a radiating element including a conductive material or a conductive pattern formed in or on a substrate (e.g., a printed circuit board (PCB)). According to an embodiment of the disclosure, the antenna module 997 may include a plurality of antennas (e.g., array antennas). In such a case, at least one antenna appropriate for a communication scheme used in the communication network, such as the first network 998 or the second network 999, may be selected, for example, by the communication module 990 (e.g., the wireless communication module 992) from the plurality of antennas. The signal or the power may then be transmitted or received between the communication module 990 and the external electronic device via the selected at least one antenna. According to an embodiment of the disclosure, another component (e.g., a radio frequency integrated circuit (RFIC)) other than the radiating element may be additionally formed as part of the antenna module 997.

According to various embodiments of the disclosure, the antenna module 997 may form a mmWave antenna module. According to an embodiment of the disclosure, the mmWave antenna module may include a printed circuit board, a RFIC disposed on a first surface (e.g., the bottom surface) of the printed circuit board, or adjacent to the first surface and capable of supporting a designated high-frequency band (e.g., the mmWave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment of the disclosure, commands or data may be transmitted or received between the electronic device 901 and the external electronic device 904 via the server 908 coupled with the second network 999. Each of the external electronic devices 902 or 904 may be a device of a same type as, or a different type, from the electronic device 901. According to an embodiment of the disclosure, all or some of operations to be executed at the electronic device 901 may be executed at one or more of the external electronic devices 902, 904, or 908. For example, if the electronic device 901 should perform a function or a service automatically, or in response to a request from a user or another device, the electronic device 901, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 901. The electronic device 901 may provide the outcome, with or without further processing of the outcome, as at least part of a reply to the request. To that end, a cloud computing, distributed computing, mobile edge computing (MEC), or client-server computing technology may be used, for example. The electronic device 901 may provide ultra low-latency services using, e.g., distributed computing or mobile edge computing. In another embodiment of the disclosure, the external electronic device 904 may include an internet-of-things (IoT) device. The server 908 may be an intelligent server using machine learning and/or a neural network. According to an embodiment of the disclosure, the external electronic device 904 or the server 908 may be included in the second network 999. The electronic device 901 may be applied to intelligent services (e.g., smart home, smart city, smart car, or healthcare) based on 5G communication technology or IoT-related technology.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used in connection with various embodiments of the disclosure, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment of the disclosure, the module may be implemented in a form of an application-specific integrated circuit (ASIC).

Various embodiments as set forth herein may be implemented as software (e.g., the program 940) including one or more instructions that are stored in a storage medium (e.g., an internal memory 936 or an external memory 938) that is readable by a machine (e.g., the electronic device 901). For example, a processor (e.g., the processor 920) of the machine (e.g., the electronic device 901) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment of the disclosure, a method according to various embodiments of the disclosure may be included and provided in a computer program product. The computer program product may be traded as a product between a seller and a buyer. The computer program product may be distributed in the form of a machine-readable storage medium (e.g., a compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments of the disclosure, each component (e.g., a module or a program) of the above-described components may include a single entity or multiple entities, and some of the multiple entities may be separately disposed in different components. According to various embodiments of the disclosure, one or more of the above-described components may be omitted, or one or more other components may be added. Alternatively or additionally, a plurality of components (e.g., modules or programs) may be integrated into a single component. In such a case, according to various embodiments of the disclosure, the integrated component may still perform one or more functions of each of the plurality of components in the same or similar manner as they are performed by a corresponding one of the plurality of components before the integration. According to various embodiments of the disclosure, operations performed by the module, the program, or another component may be carried out sequentially, in parallel, repeatedly, or heuristically, or one or more of the operations may be executed in a different order or omitted, or one or more other operations may be added.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. A wearable electronic device comprising:
a housing including a cover:
a bracket disposed in the housing and including a first part:
a printed circuit board disposed between the cover and the bracket and at least partially facing a first surface of the first part of the bracket:
a sound sensor structure disposed on a second surface that is different from the first surface of the first part of the bracket:
a biometric sensor structure installed in the cover to overlap the first surface of the first part of the bracket with respect to a direction that is perpendicular to the printed circuit board; and
a damping structure interposed between the biometric sensor structure and the printed circuit board and configured to elastically support the biometric sensor structure and the printed circuit board,
wherein the damping structure is arranged to overlap the sound sensor structure with respect to the direction that is perpendicular to the printed circuit board.

2. The wearable electronic device of claim 1, wherein the damping structure includes a first member having a repulsive force.

3. The wearable electronic device of claim 2,
wherein the damping structure includes a second member stacked on the first member, and
wherein the repulsive force of the first member is different from a repulsive force of the second member.

4. The wearable electronic device of claim 3,
wherein the first member is disposed between the biometric sensor structure and the second member, and wherein the second member is disposed between the first member and the printed circuit board.

5. The wearable electronic device of claim 3, wherein the repulsive force of the first member is lower than the repulsive force of the second member.

6. The wearable electronic device of claim 3, wherein the first member includes a sponge.

7. The wearable electronic device of claim 3, wherein the second member includes a polyethylene terephthalate film.

8. The wearable electronic device of claim 3,
wherein the printed circuit board includes a first surface facing the cover and a second surface being opposite to the first surface,
wherein the biometric sensor structure includes:
a board disposed above the first surface of the printed circuit board, and
a temperature sensor disposed in the board to face the cover,
wherein the first member is disposed between the board and the second member, and
wherein the second member is disposed between the first surface of the printed circuit board and the first member.

9. The wearable electronic device of claim 3,
wherein the damping structure includes at least two of a first bonding layer, a second bonding layer, and a third bonding layer,
wherein the first bonding layer is disposed between the biometric sensor structure and the first member,
wherein the second bonding layer is disposed between the first member and the second member, and
wherein the third bonding layer is disposed between the second member and the printed circuit board.

10. The wearable electronic device of claim 2, wherein the first member has a hollow.

11. The wearable electronic device of claim 1, further comprising:
a battery at least partially accommodated in an interior of the bracket; and
a connection member electrically connecting the battery and the printed circuit board,
wherein the housing includes a frame, to which the cover is coupled,
wherein the first part of the bracket is located between the battery and the frame,
wherein a first recess, in which the connection member is disposed, is formed on the first surface of the first part of the bracket, and
wherein a second recess, in which the sound sensor structure is at least partially accommodated, is formed on the second surface of the first part of the bracket.

12. The wearable electronic device of claim 1, further comprising:
a sensor module,
wherein the cover includes a first cover and a second cover coupled to the first cover to close a hollow formed in the first cover,
wherein the biometric sensor structure is at least partially accommodated in a through-hole formed in the first cover, wherein the sensor module is disposed on a rear surface of the second cover,
wherein the biometric sensor structure is configured to detect first biometric information including a temperature of a body of a user, which contacts the cover, through the through-hole, and
wherein the sensor module is configured to detect biometric information that is different from the first biometric information.

13. The wearable electronic device of claim 1, further comprising:
a capacitor disposed in the printed circuit board,
wherein the damping structure is located between the sound sensor structure and the capacitor with respect to a direction that is parallel to the printed circuit board.

14. The wearable electronic device of claim 13,
wherein the printed circuit board includes a part between the damping structure and the sound sensor structure with respect to a direction that is parallel to the printed circuit board, and
wherein no capacitor is disposed in the part of the printed circuit board.

15. A wearable electronic device comprising:
a housing including a cover;
a bracket disposed in the housing and including a first part:
a printed circuit board disposed between the cover and the bracket and at least partially facing a first surface of the first part of the bracket:
a sound sensor structure disposed on a second surface that is different from the first surface of the first part of the bracket; and
a damping structure,
wherein the cover includes a protrusion extending toward the printed circuit board, and
wherein the damping structure is disposed between the printed circuit board and the protrusion to elastically support the printed circuit board,
wherein the damping structure is arranged to overlap the sound sensor structure with respect to a direction parallel to the printed circuit board.

16. The wearable electronic device of claim 15, wherein the damping structure includes a first member having a repulsive force.

17. The wearable electronic device of claim 16,
wherein the damping structure includes a second member stacked on the first member, and
wherein the repulsive force of the first member is different from a repulsive force of the second member.

18. The wearable electronic device of claim 17,
wherein the first member is disposed between the protrusion and the second member, and
wherein the second member is disposed between the first member and the printed circuit board.

19. The wearable electronic device of claim 17, wherein the repulsive force of the first member is lower than the repulsive force of the second member.

* * * * *